United States Patent
Sanchez et al.

(10) Patent No.: US 12,130,391 B2
(45) Date of Patent: *Oct. 29, 2024

(54) METHODS AND APPARATUSES FOR AZIMUTHAL SUMMING OF ULTRASOUND DATA

(71) Applicant: BFLY OPERATIONS, INC., Burlington, MA (US)

(72) Inventors: Nevada J. Sanchez, Guilford, CT (US); Liewei Bao, Westford, MA (US); Tyler S. Ralston, Clinton, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/503,416

(22) Filed: Nov. 7, 2023

(65) Prior Publication Data

US 2024/0069181 A1 Feb. 29, 2024

Related U.S. Application Data

(63) Continuation of application No. 17/493,775, filed on Oct. 4, 2021, now Pat. No. 11,808,897.

(Continued)

(51) Int. Cl.
*G01S 7/52* (2006.01)
*A61B 8/00* (2006.01)
(Continued)

(52) U.S. Cl.
CPC ........ *G01S 7/52025* (2013.01); *A61B 8/4477* (2013.01); *A61B 8/4494* (2013.01);
(Continued)

(58) Field of Classification Search
CPC ....... A61B 8/54; A61B 8/4477; A61B 8/4494; A61B 8/4472; A61B 8/4236;
(Continued)

(56) References Cited

U.S. PATENT DOCUMENTS

| 7,202,941 | B2* | 4/2007 | Munro | G01S 17/10 |
| | | | | 356/5.1 |
| 7,914,442 | B1* | 3/2011 | Gazdzinski | A61B 1/00156 |
| | | | | 600/128 |

(Continued)

OTHER PUBLICATIONS

Daft et al., "Microfabricated Ultrasonic Transducers Monolithically Integrated with High Voltage Electronics," IEEE Ultrasonics Symposium conf 2004; pp. 493-496 (4 pages).

(Continued)

*Primary Examiner* — Daniel L Murphy
*Assistant Examiner* — Amie M Ndure
(74) *Attorney, Agent, or Firm* — Carter, DeLuca & Farrell LLP

(57) ABSTRACT

Aspects of the technology described herein related to controlling, using control circuitry, modulation circuitry to modulate and delay first ultrasound data generated by first ultrasound transducers positioned at a first azimuthal position of an ultrasound transducer array of an ultrasound device and second ultrasound data generated by second ultrasound transducers positioned at a second azimuthal position of the ultrasound transducer array of the ultrasound device, such that the first ultrasound data is delayed by a first delay amount and the second ultrasound data is delayed by a second delay amount that is different from the first delay amount. The first and second ultrasound data received from the modulation circuitry may be filtered and summed. The ultrasound transducer array, the control circuitry, the modulation circuitry, the filtering circuitry, and the summing circuitry may be integrated onto a semiconductor chip or one or more semiconductor chips packaged together.

14 Claims, 10 Drawing Sheets

Related U.S. Application Data

(60) Provisional application No. 63/087,518, filed on Oct. 5, 2020.

(51) Int. Cl.
*A61B 8/08* (2006.01)
*G01S 15/89* (2006.01)

(52) U.S. Cl.
CPC ........ *G01S 7/52034* (2013.01); *G01S 7/5208* (2013.01); *A61B 8/4236* (2013.01); *A61B 8/4472* (2013.01); *A61B 8/5207* (2013.01); *G01S 15/8915* (2013.01); *G01S 15/8925* (2013.01)

(58) Field of Classification Search
CPC . A61B 8/5207; G01S 7/52025; G01S 7/5208; G01S 7/52034; G01S 15/8925; G01S 15/8915

See application file for complete search history.

(56) References Cited

U.S. PATENT DOCUMENTS

| | | | |
|---|---|---|---|
| 8,068,897 B1* | 11/2011 | Gazdzinski | A61B 5/0071 600/128 |
| 8,852,103 B2 | 10/2014 | Rothberg et al. | |
| 9,067,779 B1 | 6/2015 | Rothberg et al. | |
| 9,229,097 B2 | 1/2016 | Rothberg et al. | |
| 9,242,275 B2 | 1/2016 | Rothberg et al. | |
| 9,473,136 B1 | 10/2016 | Chen et al. | |
| 9,492,144 B1 | 11/2016 | Chen et al. | |
| 9,499,392 B2 | 11/2016 | Rothberg et al. | |
| 9,505,030 B2 | 11/2016 | Rothberg et al. | |
| 9,521,991 B2 | 12/2016 | Rothberg et al. | |
| 9,533,873 B2 | 1/2017 | Rothberg et al. | |
| 9,592,030 B2 | 3/2017 | Rothberg et al. | |
| 9,592,032 B2 | 3/2017 | Rothberg et al. | |
| 9,705,518 B2 | 7/2017 | Chen et al. | |
| 9,778,348 B1 | 10/2017 | Chen et al. | |
| 10,082,488 B2 | 9/2018 | Chen et al. | |
| 10,082,565 B2 | 9/2018 | Chen et al. | |
| 10,175,347 B2 | 1/2019 | Chen et al. | |
| 10,187,020 B2 | 1/2019 | Chen et al. | |
| 10,196,261 B2 | 2/2019 | Rothberg et al. | |
| 10,624,613 B2 | 4/2020 | Ralston | |
| 10,695,034 B2 | 6/2020 | Ralston et al. | |
| 10,755,692 B2 | 8/2020 | Ralston et al. | |
| 10,840,864 B2 | 11/2020 | Singh et al. | |
| 10,856,840 B2 | 12/2020 | Rothberg et al. | |
| 10,857,567 B2 | 12/2020 | Singh et al. | |
| 10,859,687 B2 | 12/2020 | Bao et al. | |
| 10,972,842 B2 | 4/2021 | Lutsky et al. | |
| 11,005,435 B2 | 5/2021 | Singh et al. | |
| 11,048,334 B2 | 6/2021 | Rothberg et al. | |
| 11,137,486 B2 | 10/2021 | Ralston et al. | |
| 11,154,279 B2 | 10/2021 | Bao et al. | |
| 11,808,897 B2 | 11/2023 | Sanchez et al. | |
| 2001/0051766 A1* | 12/2001 | Gazdzinski | A61B 10/02 606/1 |
| 2011/0055447 A1 | 3/2011 | Costa | |
| 2011/0194176 A1* | 8/2011 | Behrend | A61B 5/0059 359/387 |
| 2011/0196222 A1* | 8/2011 | Behrend | A61B 5/0062 600/407 |
| 2011/0196239 A1* | 8/2011 | Behrend | A61B 5/0062 600/476 |
| 2012/0071710 A1* | 3/2012 | Gazdzinski | A61B 8/12 600/101 |
| 2014/0046188 A1* | 2/2014 | Yen | A61B 8/4427 600/447 |
| 2014/0243614 A1 | 8/2014 | Rothberg et al. | |
| 2015/0293214 A1* | 10/2015 | Cannon | A61B 8/4483 367/87 |
| 2017/0307741 A1 | 10/2017 | Ralston et al. | |
| 2017/0360399 A1 | 12/2017 | Rothberg et al. | |
| 2017/0360414 A1* | 12/2017 | Rothberg | A61B 8/12 |
| 2018/0070917 A1 | 3/2018 | Rothberg et al. | |
| 2018/0206821 A1* | 7/2018 | Shikata | A61B 8/54 |
| 2018/0360426 A1 | 12/2018 | Singh et al. | |
| 2019/0000422 A1 | 1/2019 | West et al. | |
| 2019/0001159 A1 | 1/2019 | Chen et al. | |
| 2019/0069842 A1 | 3/2019 | Rothberg et al. | |
| 2019/0142387 A1 | 5/2019 | Chen et al. | |
| 2019/0282207 A1 | 9/2019 | Chen et al. | |
| 2019/0307428 A1 | 10/2019 | Silberman et al. | |
| 2019/0343484 A1 | 11/2019 | Rothberg et al. | |
| 2020/0008709 A1 | 1/2020 | Martin et al. | |
| 2020/0184176 A1 | 6/2020 | Liu et al. | |
| 2020/0205670 A1 | 7/2020 | Ralston et al. | |
| 2020/0315586 A1* | 10/2020 | Sanchez | G01S 7/52026 |
| 2020/0315592 A1 | 10/2020 | Soleimani et al. | |
| 2020/0348794 A1 | 11/2020 | Ralston et al. | |
| 2020/0349342 A1 | 11/2020 | Ralston et al. | |
| 2020/0383660 A1 | 12/2020 | Rothberg et al. | |
| 2020/0390419 A1 | 12/2020 | Neben et al. | |
| 2020/0405266 A1 | 12/2020 | Yang et al. | |
| 2020/0405267 A1 | 12/2020 | Yang et al. | |
| 2020/0405271 A1 | 12/2020 | Chiu et al. | |
| 2021/0028792 A1 | 1/2021 | Hwang et al. | |
| 2021/0056041 A1 | 2/2021 | Sanchez | |
| 2021/0088638 A1 | 3/2021 | Chen et al. | |
| 2021/0093291 A1 | 4/2021 | Sanchez | |
| 2021/0167791 A1 | 6/2021 | Hwang et al. | |
| 2021/0183832 A1 | 6/2021 | Chen et al. | |
| 2021/0325349 A1 | 10/2021 | Chen et al. | |
| 2021/0328564 A1 | 10/2021 | Chen et al. | |
| 2021/0330295 A1 | 10/2021 | Soleimani et al. | |

OTHER PUBLICATIONS

Daft et al., "A matrix Transducer Design with Improved Image Quality and Acquisition Rate," IEEE Ultrasonics Symposium conf 2007; pp. 411-415 (5 pages).

Gurun et al., "Front-end CMOS Electronics for Monolithic Integration with CMUT Arrays: Circuit Design and Initial Experimental Results," IEEE Ultrasonics Symposium, 2008, pp. 390-393 (4 pages).

Gurun et al., "Front-End Receiver Electronics for High-Frequency Monolithic CMUT-on-CMOS Imaging Arrays," IEEE Trans on Ultrason, Ferroelectr, Freq Control, Aug. 2011; 58 (8): 1658-68 (11 pages).

* cited by examiner

METHODS AND APPARATUSES FOR AZIMUTHAL SUMMING OF ULTRASOUND DATA

CROSS-REFERENCE TO RELATED APPLICATIONS

This application is a continuation of U.S. application Ser. No. 17/493,775 filed on Oct. 4, 2021, now U.S. Pat. No. 11,808,897, which claims the benefit of, and priority to, U.S. Provisional Patent Application Ser. No. 63/087,518 filed on Oct. 5, 2020. The entire contents of the foregoing applications are incorporated by reference herein.

FIELD

Generally, the aspects of the technology described herein relate to processing ultrasound data. Certain aspects relate to azimuthal summing of ultrasound data.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the application, an ultrasound device includes: an ultrasound transducer array including first ultrasound transducers positioned at a first azimuthal position of the ultrasound transducer array and second ultrasound transducers positioned at a second azimuthal position of the ultrasound transducer array; modulation circuitry; control circuitry configured to control the modulation circuitry to modulate and delay first ultrasound data generated by the first ultrasound transducers and second ultrasound data generated by the second ultrasound transducers such that the first ultrasound data is delayed by a first delay amount and the second ultrasound data is delayed by a second delay amount that is different from the first delay amount; filtering circuitry configured to filter the first and second ultrasound data received from the modulation circuitry; and summing circuitry configured to sum the first and second ultrasound data received from the filtering circuitry. The ultrasound transducer array, the control circuitry, the modulation circuitry, the filtering circuitry, and the summing circuitry are integrated onto a semiconductor chip or one or more semiconductor chips packaged together using semiconductor chip packaging technology.

In some embodiments, the modulation circuitry includes a multiplier a direct digital synthesis (DDS) circuitry. In some embodiments, the control circuitry is configured, when controlling the modulation circuitry to modulate and delay the first ultrasound data generated by the first ultrasound transducers and the second ultrasound data generated by the second ultrasound transducers such that the first ultrasound data is delayed by the first delay amount and the second ultrasound data is delayed by the second delay amount, to control the modulation circuitry to multiply the first ultrasound data by $e^{-i\omega_{DDS}(t-\tau_1)}$ and multiply the second ultrasound data by $e^{-i\omega_{DDS}(t-\tau_2)}$, where $\tau_1$ is the first delay amount, $\tau_2$ is the second delay amount, $\omega_{DDS}$ is a center frequency, and t is a time variable. In some embodiments, the first delay amount is a sum of two delays, one delay corresponding to an elevational position of the ultrasound transducer array from which the first ultrasound data was generated and one delay corresponding to the first azimuthal position of the ultrasound transducer array.

In some embodiments, the control circuitry is configured, when controlling the modulation circuitry to modulate and delay the first ultrasound data generated by the first ultrasound transducers and the second ultrasound data generated by the second ultrasound transducers such that the first ultrasound data is delayed by the first delay amount and the second ultrasound data is delayed by the second delay amount, to control the modulation circuitry to implement a relative phase shift between the first ultrasound data and the second ultrasound data.

In some embodiments, the control circuitry is configured, when controlling the modulation circuitry to modulate and delay the first ultrasound data generated by the first ultrasound transducers and the second ultrasound data generated by the second ultrasound transducers such that the first ultrasound data is delayed by the first delay amount and the second ultrasound data is delayed by the second delay amount, to retrieve the first delay amount and the second delay amount from delay register storage circuitry integrated onto the semiconductor chip or the one or more semiconductor chips packaged together on a semiconductor chip package. In some embodiments, the ultrasound device is configured to receive the first delay amount and the second delay amount from an external computing device.

In some embodiments, the ultrasound device is configured to use the first delay amount for every elevational position at the first azimuthal position of the ultrasound transducer array and to use the second delay amount for every elevational position at the second azimuthal position of the ultrasound transducer array. In some embodiments, the ultrasound device further includes circuitry configured to rotate a delay profile across the ultrasound transducer array by a certain number of degrees. In some embodiments, the ultrasound device is configured to perform multiplane imaging by using the delay profile for imaging along a first imaging plane, rotating the delay profile, and using the rotated delay profile for imaging along a second imaging plane. In some embodiments, the summing circuitry is further configured to perform noise shaping when summing the first and second ultrasound data.

In some embodiments, the first ultrasound transducers are positioned at the first azimuthal position and different elevational positions of the ultrasound transducer array, and the first ultrasound data includes a stream of data having, at a given time, a value of ultrasound data from a subset of the first ultrasound transducers at one elevational position of the different elevational positions. In some embodiments, the ultrasound device is configured to transmit an output of the summing circuitry off the semiconductor chip or the one or more semiconductor chips packaged together.

Other aspects of the application include a method for performing the functions of the ultrasound device described above.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
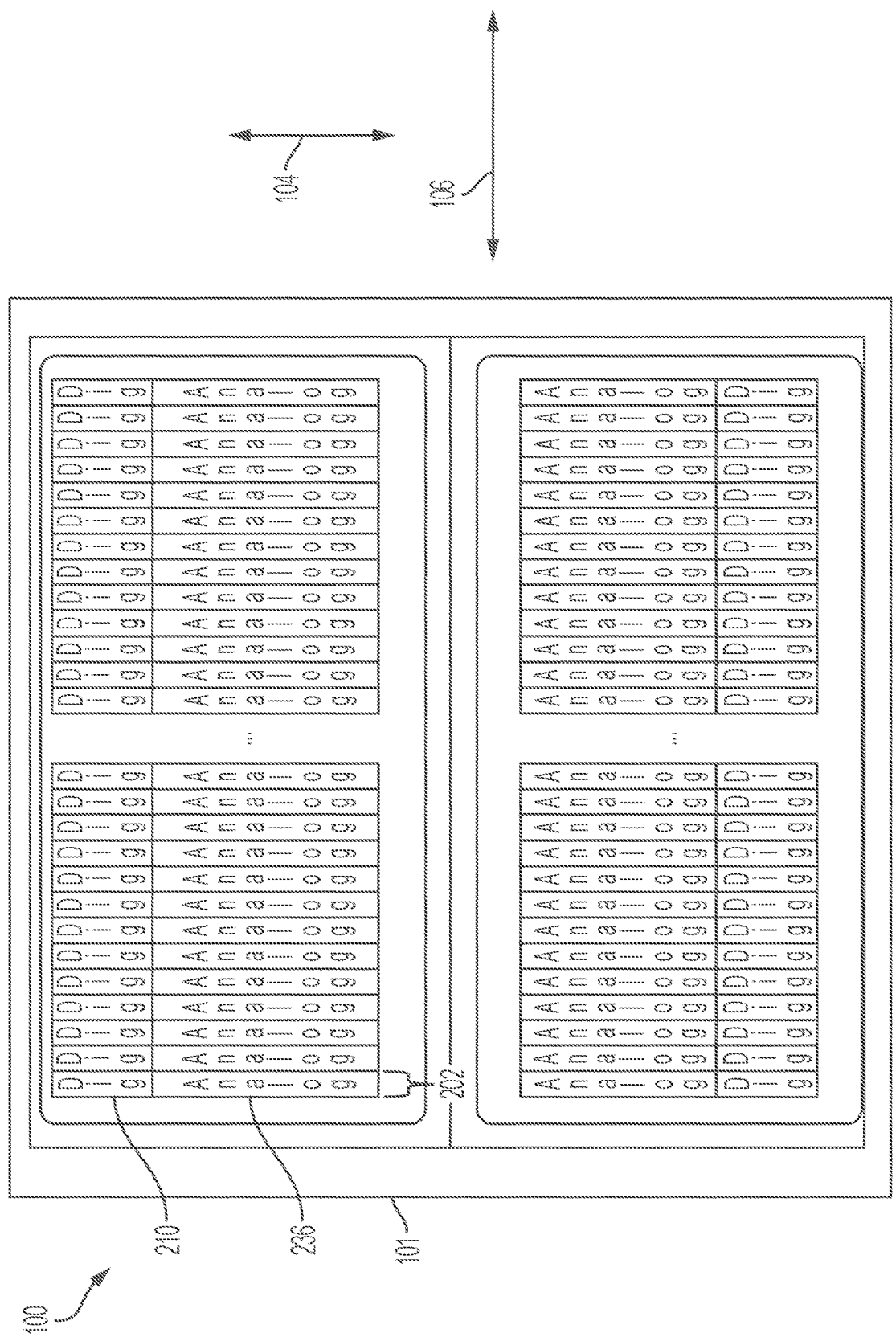
FIG. 1 illustrates an example physical layout of a portion of an ultrasound-on-chip, in accordance with certain embodiments described herein.

Recent advances in ultrasound technology have enabled large arrays of ultrasound transducers and ultrasound processing units (UPUs) to be integrated onto a semiconductor chip or one or more semiconductor chips packaged together (e.g., in a stacked configuration) to form an ultrasound-on-chip. Each UPU may include integrated circuitry including, for example, one or more of high-voltage pulsers to drive the ultrasonic transducers to emit ultrasound waves; analog and mixed-signal receiver channels to receive and digitize ultrasound echoes; digital processing circuitry to filter, compress, and/or beamform the digital data from each channel; and digital sequencing circuitry to control and synchronize different parts of the circuitry. An ultrasound-on-chip may form the core of an ultrasound device, which may be in the form, for example, of a handheld ultrasound probe, a wearable ultrasound patch, or an ingestible ultrasound pill. For further description of ultrasound-on-chips and ultrasound systems, see U.S. patent application Ser. No. 15/626,711 titled "UNIVERSAL ULTRASOUND DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

Certain imaging techniques may require beamforming of ultrasound data along the azimuthal dimension and/or elevational dimension of an ultrasound transducer array. After transmission of an ultrasound pulse into a subject, beamforming may include applying different delays to ultrasound data collected by different ultrasound transducers and then summing the delayed ultrasound data. Conventional beamforming may be performed on a host device to which an ultrasound probe is coupled, with the ultrasound probe and the host forming at least part of an ultrasound system. In other words, the ultrasound probe may transmit the ultrasound data to the host device, which may then perform the delaying and summing. However, the amount of data that the ultrasound probe may need to transmit to the host device after each pulse emitted by the ultrasound transducer array may be large. For example, if the host device needs to individually apply delays to n sets of ultrasound data for beamforming after each pulse, then the ultrasound probe may need to individually transmit each of the n sets of ultrasound data to the host device. Transferring such a large amount of data from the probe to the host may be impractical or entirely unworkable for large ultrasound transducer arrays, where medically relevant pulse repetition frequencies (PRF) are desired.

The technique of microbeamforming may include performing certain delaying and summing on the ultrasound probe itself. This may help to reduce the amount of data that the ultrasound probe may need to transmit to the host device after each pulse. For example, if the ultrasound probe applies delays to n sets of ultrasound data and then sums pairs of delayed ultrasound data, then the ultrasound probe may only need to individually transmit n/2 sets of ultrasound data to the host device. Further beamforming may be performed at the host device. Reducing the amount of data that the ultrasound probe needs to transmit to the host device after each pulse may help to increase the pulse repetition frequency (PRF) that the ultrasound system is capable of achieving. Higher PRF may improve the ultrasound imaging by enabling faster frame rates, improved lateral resolution, and/or improved axial resolution. Additionally, higher PRF may improve temporal resolutions between pulses/excitations. Higher temporal resolutions may improve the performance of Doppler imaging to increase the range of measurable velocities and accelerations. Also, higher temporal resolutions may improve contrast by increasing SNR.

In the context of an ultrasound-on-chip, microbeamforming may include performing delaying and summing on the ultrasound-on-chip, such that the amount of data that the ultrasound device containing the ultrasound-on-chip must transmit off-chip to a downstream electronic device (e.g., a field-programmable gate array (FPGA) or another semiconductor chip configured to perform further processing of ultrasound data) may be reduced. The inventors have recognized that receive circuitry that is already part of the datapath of an ultrasound-on-chip may be augmented with control circuitry to implement microbeamforming on the ultrasound-on-chip. According to at least some aspects, the microbeamforming may include delaying and summing ultrasound data generated by ultrasound transducers positioned at adjacent positions along the azimuthal dimension of the ultrasound-on-chip. The receive circuitry may include control circuitry configured to control modulation circuitry to modulate and delay ultrasound data generated by one or more ultrasound transducers positioned at one azimuthal position along the azimuthal dimension of the ultrasound transducer array and ultrasound data generated by one or more ultrasound transducers positioned at another azimuthal position, such that the ultrasound data from the different azimuthal positions is delayed by different amounts. It should be appreciated that azimuthal position may refer to a physical position on the ultrasound transducer array along the scan direction. It should also be appreciated that multiple ultrasound transducers may be considered to be positioned at one azimuthal position if the ultrasound transducers contribute to generating a single ultrasound data point associated with that azimuthal position.

In some embodiments the modulation is realized by the receive circuitry introducing a phase offset into the oscillator of a direct digital synthesis (DDS) circuit, such that the phase offset compensates for the phase difference between a sampled time and a desired delayed sample time. Introduction of the phase offset may provide a good approximation of a delayed signal for several phase cycles in an oversampled signal bandwidth. The modulated and delayed data may be filtered by filtering circuitry and summed by summing circuitry. Summing ultrasound data from different positions along the azimuthal dimension of the ultrasound transducer array of the ultrasound-on-chip may be referred to herein as azimuthal summing.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

As referred to herein, when an output of one block of circuitry is "coupled" to an input of another block of circuitry, it should be appreciated that the two blocks of circuitry may be directly coupled together or that there may be other blocks of circuitry disposed between the two blocks of circuitry.

FIG. 1 illustrates an example physical layout of a portion of an ultrasound-on-chip 100, in accordance with certain embodiments described herein. The ultrasound-on-chip 100 is illustrated in FIG. 1 from a bird's-eye-view. FIG. 1 illustrates the ultrasound-on-chip 100, which includes a semiconductor chip 101 on which are integrated multiple ultrasound processing units (UPUs) 202. FIG. 1 further illustrates an elevational dimension 104 of an ultrasound transducer array (e.g., the ultrasound transducer array 256 illustrated in FIG. 2) of the ultrasound-on-chip 100, and an azimuthal dimension 106 of the ultrasound transducer array of the ultrasound-on-chip 100. Each UPU 202 may be a self-contained ultrasound processing unit that forms a sub-array of a complete ultrasound imaging array in a scalable fashion. Each UPU 202 includes an analog portion 236 and a digital portion 210 and may include, for example, any or all of high-voltage pulsers to drive ultrasonic transducers to emit ultrasound; analog and mixed-signal receiver channels to receive and digitize ultrasound echoes; digital processing circuitry to filter, compress, and/or beamform the digital data from each channel; and digital sequencing circuitry to control and synchronize different parts of the circuitry. FIG. 1 illustrates how multiple UPUs 202 are tiled along an azimuthal dimension 106 of the ultrasound-on-chip 100, and how two rows of the tiled UPUs 202 are arranged along the elevational dimension 104 of the ultrasound-on-chip 100. Ultrasound transducers of the ultrasound transducer array (not shown in FIG. 1) may be physically located on top of (i.e., with respect to the depth dimension of the ultrasound-on-chip 100, out of the plane of FIG. 1) the analog portion of each UPU 202, along the elevational dimension 104 and the azimuthal dimension 106 of the ultrasound transducer array. The arrangement of the ultrasound transducers in an array having an azimuthal dimension 106 and an elevational dimension 104 may allow for azimuthal and elevational beamforming of ultrasound signals received by the ultrasound transducers of the ultrasound-on-chip 100. In the example of FIG. 1, the ultrasound transducers and the UPUs 202 are integrated onto the semiconductor chip 101. In some embodiments, the ultrasound transducers and certain circuitry of the UPUs 202 may be integrated on one semiconductor chip while other circuitry of the UPUs 202 may be integrated onto one or more semiconductor chips. The semiconductor chips may be packaged together (e.g., in a stacked configuration, such as a configuration using an integrated fan-out (InFO) package) to form the ultrasound-on-chip 100.

The physical layout of the ultrasound-on-chip 100 as illustrated in FIG. 1 is non-limiting. For example, in some embodiments, the ultrasound-on-chip 100 may have fewer UPUs 202 than shown, more or fewer UPUs 202 in each row than shown, and/or more or fewer rows of UPUs 202 than shown. Additionally, the ultrasound-on-chip 100 may include more circuitry than the UPUs 202 shown.

Figure 2:
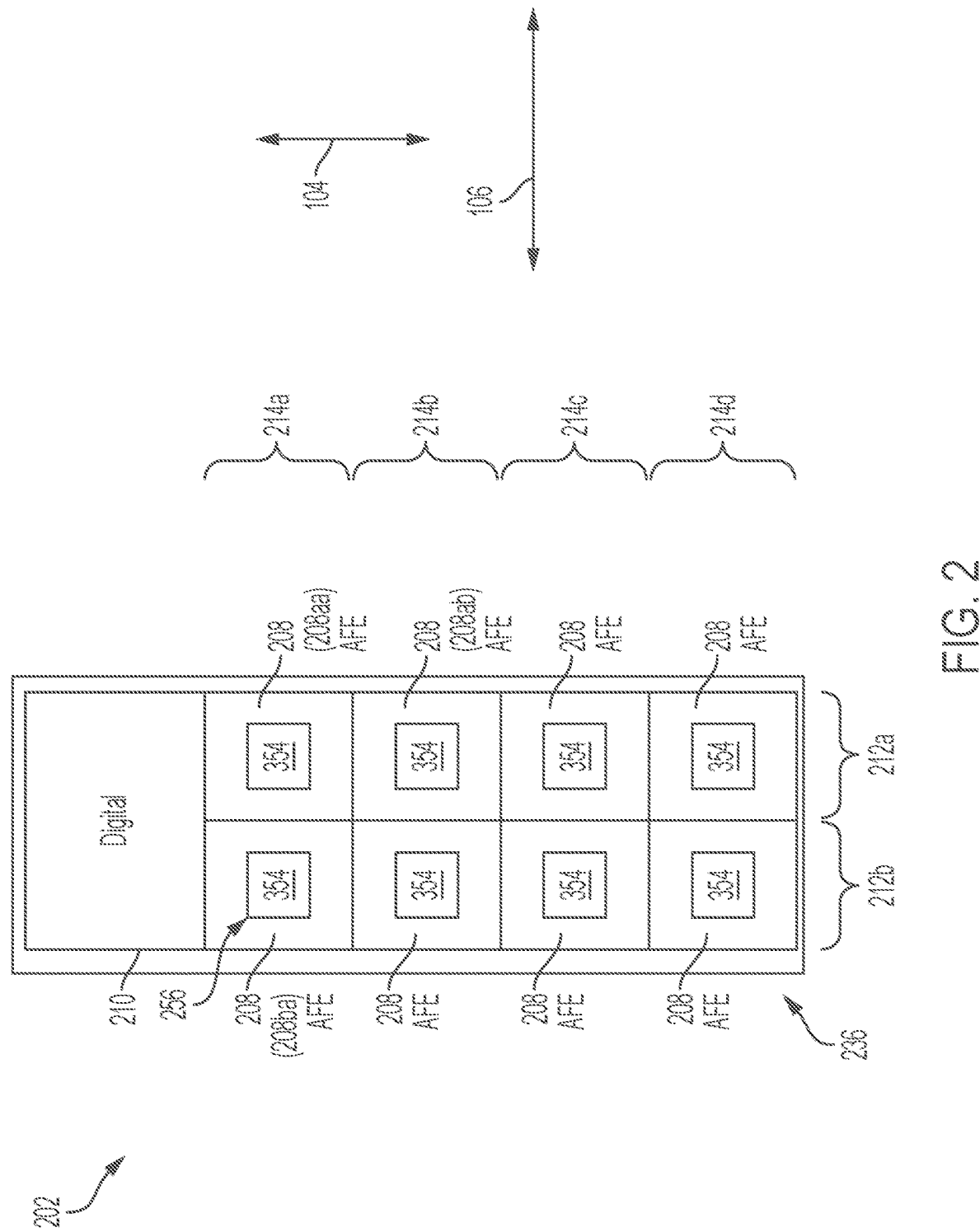
FIG. 2 illustrates an example physical layout of an ultrasound processing unit (UPU) of the ultrasound-on-chip of FIG. 1, in accordance with certain embodiments described herein.

FIG. 2 illustrates an example physical layout of an ultrasound processing unit (UPU) 202 of the ultrasound-on-chip 100 of FIG. 1, in accordance with certain embodiments described herein. The UPU 202 is illustrated in FIG. 2 from a bird's-eye-view of the ultrasound-on-chip 100. The UPU 202 includes the analog portion 236 having eight analog front-ends (AFE) 208, a digital portion 210 having digital circuitry, and an ultrasound transducer array 256 including ultrasound transducers 354 (which may be, for example, capacitive micromachined ultrasound transducers (CMUTs), piezoelectric micromachined ultrasound transducers (PMUTs), or other types of MUTs). Each of the AFEs 208 may include, among other circuitry, a pulser, a switch, analog processing circuitry (e.g., the analog processing circuitry 352a, 352b shown in FIG. 3A), and an ADC (e.g., the ADC 318a, 318b shown in FIG. 3A). It should be appreciated that in the examples of FIGS. 1 and 2, ultrasound transducer array and the UPU 202 (as well as all the UPUs 202 illustrated in FIG. 1) are integrated onto the semiconductor chip 101. In some embodiments, the ultrasound transducers and certain circuitry of the UPU 202 (as well as certain may be integrated on one semiconductor chip while other circuitry of the UPU 202 may be integrated onto one or more semiconductor chips. The semiconductor chips may be packaged together (e.g., in a stacked configuration, such as a configuration using an integrated fan-out (InFO) package) to form the ultrasound-on-chip 100. Three of the AFEs 208 are labeled with unique reference numbers for later description.

The ultrasound transducer array 256 comprises ultrasound transducers 354 physically arranged at two different positions along the azimuthal dimension 106 of the ultrasound transducer array 256, an azimuthal position 212a and an azimuthal position 212b, and at four different positions along the elevational dimension 104 of the ultrasound transducer array 256, an elevational position 214a, an elevational position 214b, an elevational position 214c, and an elevational position 214d. Each instance of the reference number 354 in FIG. 2 may represent a single ultrasound transducer or multiple ultrasound transducers coupled together such that a combined electrical output signal is generated for the corresponding AFE at that location. Thus, in some embodiments, each AFE has multiple ultrasound transducers associated therewith, and the ultrasound transducers of the various AFEs combine to form the ultrasound transducer array 256. The ultrasound transducers 354 may be physically located on top of (i.e., with respect to the depth dimension of the ultrasound-on-chip 100, out of the plane of FIG. 2) each of the AFEs 208. The ultrasound transducer 354 on top of each AFE 208 may be coupled to that AFE 208, such that the AFE 208 may be configured to process ultrasound signals from that ultrasound transducer 354.

While FIG. 2 illustrates four elevational positions 214a-214d at each of the azimuthal positions 212a and 212b of the ultrasound transducer array 256, this is not limiting, and there may be a different number of elevational positions at each of the azimuthal positions. While FIG. 2 illustrates ultrasound transducers 354 positioned at two azimuthal positions 212a and 212b for each UPU 202, this is not limiting, and there may be AFEs 208 at a different number of azimuthal positions for each UPU 202. As a particular example, while FIG. 2 illustrates a UPU 202 with dimensions 4×2, a UPU may have dimensions 3×3. It should be appreciated that the ultrasound transducer array 256 may include ultrasound transducers 354 located on top of multiple or all of the UPUs 202 in the ultrasound-on-chip 100, and thus the ultrasound transducer array 256 may be larger than illustrated in FIG. 2. In other words, FIG. 2 may only illustrate a portion of the ultrasound transducer array 256.

Figure 3A:
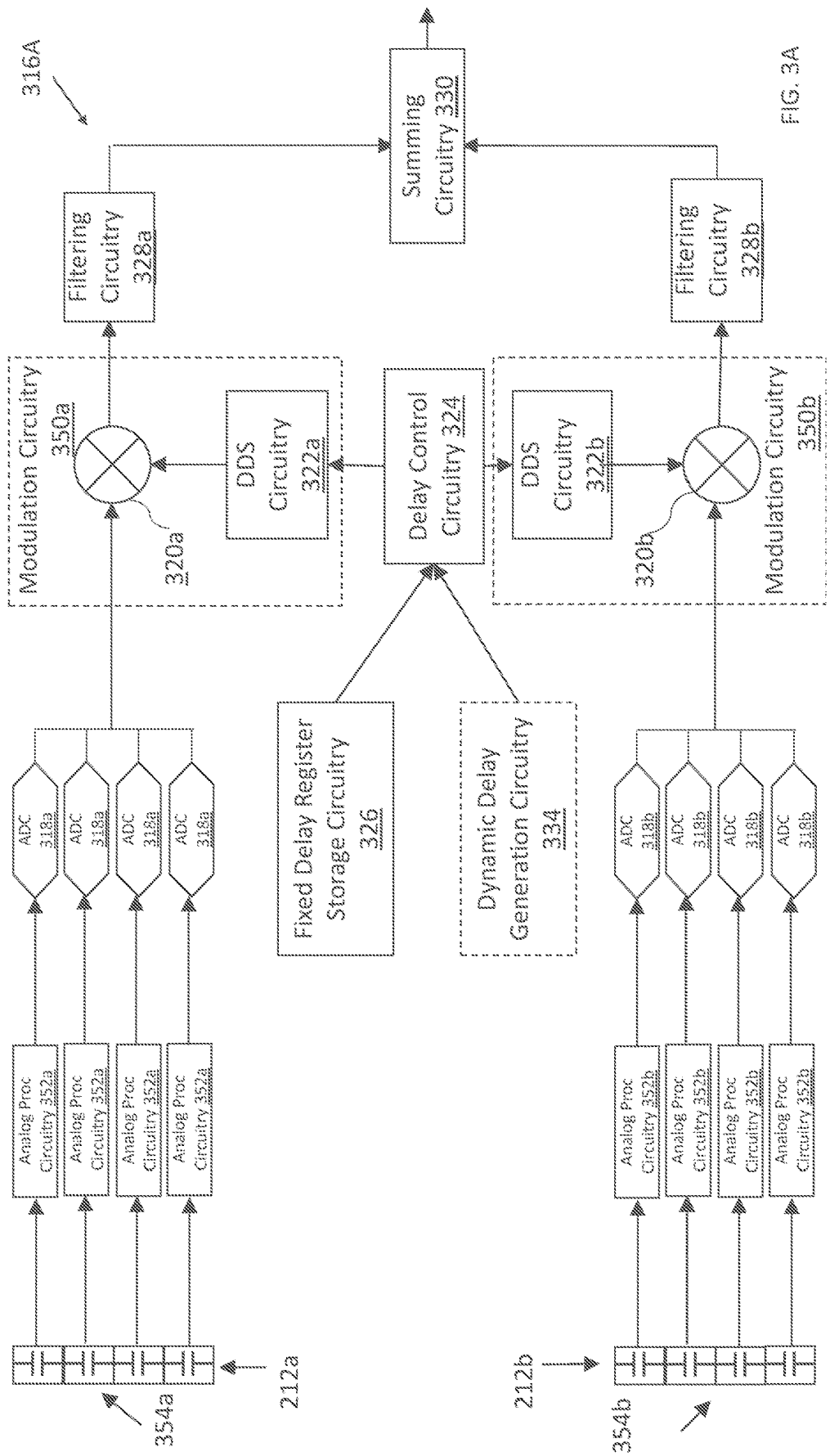
FIG. 3A is a block diagram illustrating example receive circuitry in an ultrasound device, in accordance with certain embodiments described herein.

FIG. 3A is a block diagram illustrating example receive circuitry 316A in an ultrasound device, in accordance with certain embodiments described herein. The receive circuitry 316A includes ultrasound transducers 354a, ultrasound transducers 354b, analog processing circuitry 352a, analog processing circuitry 352b, analog-to-digital converters (ADCs) 318a, ADCs 318b, modulation circuitry 350a, modulation circuitry 350b, delay control circuitry 324, fixed delay register storage circuitry 326, dynamic delay generation circuitry 334, filtering circuitry 328a, filtering circuitry 328b, and summing circuitry 330. The modulation circuitry 350a includes a multiplier 320a and direct digital synthesis (DDS) circuitry 322a, and the modulation circuitry 350b includes a multiplier 320b and DDS circuitry 322b. In some embodiments, the analog processing circuitry 352a and 352b and the ADCs 318a and 318b may be part of the analog portion 236 of a UPU 202 of the ultrasound-on-chip 100. The modulation circuitry 350a and modulation circuitry 350b, the delay control circuitry 324, the fixed delay register storage circuitry 326, the dynamic delay generation circuitry 332, the filtering circuitry 328a and 328b, and the summing circuitry 330 may be part of the digital portion 210 of the UPU 202 of the ultrasound-on-chip 100. It should be appreciated that in some embodiments, all the receive circuitry 316A as well as the ultrasound transducers 354a and 354b may be integrated onto the semiconductor chip 101. In some embodiments, the ultrasound transducers 345a and 354b and certain portions of the receive circuitry 316A may be integrated on one semiconductor chip while other portions of the receive circuitry 316A may be integrated on one or more semiconductor chips packaged together (e.g., in a stacked configuration, such as a configuration using an integrated fan-out (InFO) package) that constitute the ultrasound-on-chip 100. The receive circuitry 316A may thus be implemented as integrated circuitry.

The output of each of the ultrasound transducers 354a is coupled to an input of a block of analog processing circuitry 352a. The output of each block of analog processing circuitry 352a is coupled to an input of an ADC 318a. The output of each ADC 318a is coupled to a first input of the multiplier 320a (e.g., by multiplexing). The output of the DDS circuitry 322a is coupled to a second input of the multiplier 320a. The output of the multiplier 320a is coupled to the input of the filtering circuitry 328a. The output of each of the ultrasound transducers 354b is coupled to an input of a block of analog processing circuitry 352b. The output of each block of analog processing circuitry 352b is coupled to an input of an ADC 318b. The output of each ADC 318b is coupled to a first input the multiplier 320b. The output of the DDS circuitry 322b is coupled to a second input of the multiplier 320b. The output of the multiplier 320b is coupled to the input of the filtering circuitry 328b. The outputs of the filtering circuitry 328a and the filtering circuitry 328b are coupled to inputs of the summing circuitry 330. The fixed delay register storage circuitry 326 is coupled to the delay control circuitry 324. The dynamic delay generation circuitry 334 is coupled to the delay control circuitry 324. The delay control circuitry 324 is coupled to the DDS circuitry 322a and the DDS circuitry 322b.

The ultrasound transducers 354a and the ultrasound transducers 354b may be configured to emit pulsed ultrasonic signals into a subject, such as a patient, in response to driving signals received from pulsers (not illustrated). The pulsed ultrasonic signals may be back-scattered from structures in the subject, such as blood cells or muscular tissue, to produce echoes that return to the ultrasound transducers 354a and 354b. The ultrasound transducers 354a and 354b may be configured to convert these acoustic echoes into electrical signals (referred to herein as analog ultrasound signals). The electrical signals may be current signals. It should be appreciated that each of the four ultrasound transducers 354a and each of the four ultrasound transducers 354b may constitute more than one ultrasound transducers coupled together, such that the current outputs of each element may add together prior to being processed by the analog processing circuitry 352a and 352b, respectively. Each of the ultrasound transducers 354a may be at a different one of the elevational positions 214a-214d of the ultrasound transducer array 256 and each of the ultrasound transducers 354b may be at a different one of the elevational positions 214a-214d of the ultrasound transducer array 256.

The analog processing circuitry 352a and 352b may be configured to perform processing in the analog domain on the analog ultrasound signals output by the ultrasound transducers 354a and 354b, respectively. The analog processing circuitry 352a and 352b may include, for example, one or more analog amplifiers, one or more analog filters, one or more analog polarity converters, analog compression circuitry, analog expansion circuitry, analog beamforming circuitry, analog dechirp circuitry, analog quadrature demodulation (AQDM) circuitry, analog time delay circuitry, analog phase shifter circuitry, analog summing circuitry, analog time gain compensation circuitry, and/or analog averaging circuitry.

The ADCs 318a and 318b may be configured to convert analog ultrasound signals from the analog processing circuitry 352a and 352b, respectively, into digital ultrasound signals. In some embodiments, the analog processing circuitry 352a and 352b may be absent, and the ADCs 318a and 318b may directly convert the ultrasound signals generated by the ultrasound transducers 354a and 354b.

The ultrasound transducers 354a are positioned at the azimuthal position 212a of the ultrasound transducer array 256. Thus, the analog processing circuitry 352a and the ADCs 318a may be configured to process analog signals generated by the ultrasound transducers 354a positioned at the azimuthal position 212a of the ultrasound transducer array 256. The analog processing circuitry 352a and the ADCs 318a may be part of the AFEs 208 at the azimuthal position 212a of the ultrasound transducer array 256. In some embodiments, each block of analog processing circuitry 352a and each of the ADCs 318a may be part of one of the AFEs 208 at the azimuthal position 212a of the ultrasound transducer array 256. In some embodiments, each block of analog processing circuitry 352a and each of the ADCs 318a may be configured to process ultrasound data from a subset of the ultrasound transducers 354a at the same azimuthal position 212a but different elevational positions 214a-214d of the ultrasound transducers array 256. While FIG. 3A illustrates four ultrasound transducers 354a, four blocks of analog processing circuitry 352a, and four ADCs 318a for the azimuthal position 212a of the ultrasound transducer array 256, this is non-limiting, and there may be more than four or fewer than four of each for the azimuthal position 212a.

The ultrasound transducers 354b are positioned at the azimuthal position 212b of the ultrasound transducer array 256. Thus, the analog processing circuitry 352b and the ADCs 318b may be configured to process analog signals generated by the ultrasound transducers 354b positioned at the azimuthal position 212b of the ultrasound transducer array 256. The analog processing circuitry 352b and the ADCs 318b may be part of the AFEs 208 at the azimuthal position 212b of the ultrasound transducer array 256. In some embodiments, each block of analog processing circuitry 352b and each of the ADCs 318b may be part of one of the AFEs 208 at the azimuthal position 212b of the ultrasound transducer array 256. In some embodiments, each block of analog processing circuitry 352b and each of the ADCs 318b may be configured to process ultrasound data from a subset of the ultrasound transducers 354b at the same azimuthal position 212b but different elevational positions 214a-214d of the ultrasound transducer array 256. While FIG. 3A illustrates four ultrasound transducers 354b, four blocks of analog processing circuitry 352b, and four ADCs 318b for the azimuthal position 212b of the ultrasound transducer array 256, this is non-limiting, and there may be more than four or fewer than four of each for the azimuthal position 212b.

The ultrasound data output from the ADCs 318a and the ADCs 318b may be in the form of a stream of serial ultrasound data from different ADCs. For example, the value of a stream from the ADCs 318a at one time may be the value of digitized ultrasound data from one of the ADCs 318a, while the value of the stream from the ADCs 318a at a different time may be the value of digitized ultrasound data from a different one of the ADCs 318a. When different ADCs 318a process ultrasound data from ultrasound transducers 354a at different elevational positions 214b of the ultrasound transducer array 256, the value of a stream from the ADCs 318a at one time may be the value of digitized ultrasound data from a subset of the ultrasound transducers 354a that are positioned at one of the elevational positions 214a-214d, while the value of the stream from the ADCs 318a at a different time may be the value of digitized ultrasound data from a different subset of the ultrasound transducers 354a that are positioned at a different one of the elevational positions 214a-214d. In some embodiments, the ultrasound data may pipeline out of the ADCs 318a and the ADCs 318b as serial streams. As described above, the ADCs 318a may be configured to process ultrasound data generated by the ultrasound transducers 354a positioned at the azimuthal position 212a of the ultrasound transducer array 256, and the ADCs 318b may be configured to process ultrasound data generated by the ultrasound transducers 354b positioned at the azimuthal position 212b of the ultrasound transducer array 256. Thus, the output from the ADCs 318a may include a stream of ultrasound data from the ultrasound transducers 354a positioned at the azimuthal position 212a of the ultrasound transducer array 256 that has been processed in the analog domain (by the analog processing circuitry 352a) and digitized. The output from the ADCs 318b may include a stream of the ultrasound data from the ultrasound transducers 354b positioned at the azimuthal position 212b of the ultrasound transducer array 256 that has been processed in the analog domain (by the analog processing circuitry 352b) and digitized. The downstream multipliers 320a and 320b, filtering circuitry 328a and 328b, and summing circuitry 330 may operate on ultrasound data in stream form.

The modulation circuitry 350a and the modulation circuitry 350b may be configured to translate the frequency of the ultrasound data from the ADCs 318a and the ADCs 318b, respectively. For example, if the ultrasound data from the ADCs 318a occupies a certain band of frequencies, the modulation circuitry 350a may be configured to modulate the ultrasound data from the ADCs 318a such that it occupies a different band of frequencies, for example a band of frequencies with a lower center frequency. The DDS circuitry 322a and the DDS circuitry 322b may be configured to generate digital sinusoidal waveforms for forming a complex signal $e^{-i\omega_{DDS}t}$, where $\omega_{DDS}=2\pi f_{DDS}$ is the center frequency of interest and t is the time variable. To generate these digital sinusoidal waveforms, the DDS circuitry 322a and the DDS circuitry 322b may each include one or more DDS phase counters. The value of a DDS phase counter may be used in sine and/or cosine lookup table (LUT) circuits to generate the sine and cosine portions of the complex signal $e^{-i\omega_{DDS}t}$. The increment value of a DDS phase counter may be proportional to $1/\omega_{DDS}$. In some embodiments, a coordinate rotation digital computer (CORDIC) may be used to generate the sine and cosine portions.

The multiplier 320a may be configured to multiply the ultrasound data from the ADCs 318a with the complex signal $e^{-i\omega_{DDS}t}$ using the sinusoidal waveforms generated by the DDS circuitry 322a. The multiplier 320b may be configured to multiply the ultrasound data from the ADCs 318b with the complex signal $e^{-i\omega_{DDS}t}$ using the sinusoidal waveforms generated by the DDS circuitry 322b. To realize this multiplication, the multiplier 320a and the multiplier 320b may use quadrature modulation.

For narrow band signals or small delays $\tau$, $f(t-\tau) \approx e^{-i\omega\tau}f(t)$. In other words, a delay $\tau$ of a signal $f(t)$ may be implemented by multiplying $f(t)$ by $e^{-i\omega\tau}$. As described above, the modulation circuitry 350a and the modulation circuitry 350b may already be configured to multiply ultrasound data by $e^{i\omega_{DDS}t}$ in order to perform modulation. The delay control circuitry 324 may be configured to control the modulation circuitry 350a and 350b such that, when performing the modulation, they also implement delays. Thus, instead of multiplying ultrasound data by $e^{-i\omega_{DDS}t}$, as would be done for simple modulation, the modulation circuitry may be configured to multiply ultrasound data by $e^{-i\omega_{DDS}(t-\tau)}$ to implement a delay while performing modulation. In some embodiments, the delay control circuitry 324 may control the DDS circuitry 322a and 322b to add different offsets to the waveforms used for multiplication with different ultrasound data, so that, for example, some ultrasound data is multiplied by $e^{-i\omega_{DDS}(t-\tau_1)}$ and some ultrasound data is instead multiplied by $e^{-i\omega_{DDS}(t-\tau_2)}$. As described above, the output of the ADCs 318a may be a stream of the ultrasound data from the ultrasound transducers 354a positioned at the azimuthal position 212a of the ultrasound transducer array 256 that has been processed in the analog domain and digitized, and the output of the ADCs 318b may be a stream of the ultrasound data from the ultrasound transducers 354b positioned at the azimuthal position 212b of the ultrasound transducer array 256 that has been processed in the analog domain and digitized. Thus, the output from the modulation circuitry 350a may include a stream of the ultrasound data from the ultrasound transducers 354a positioned at the azimuthal position 212a of the ultrasound transducer array 256 that has been processed in the analog domain, digitized, modulated, and delayed, and the output from the modulation circuitry 350b may include a stream of the ultrasound data from the ultrasound transducers 354b positioned at the azimuthal position 212b of the ultrasound transducer array 256 that has been processed in the analog domain, digitized, modulated, and delayed.

In some embodiments, the delay control circuitry 324 may be configured to control the modulation circuitry 350a and 350b to add different phase offsets to ultrasound data generated by ultrasound transducers 354 positioned at different elevational positions as well as different phase offsets to ultrasound data generated by ultrasound transducers 354 positioned at different azimuthal positions. Regarding adding different phase offsets to ultrasound data from different elevational positions, the delay control circuitry 324 may be configured to control the DDS circuitry 322a to add different phase offsets to the complex signals generated by the DDS circuitry 322a for multiplying, using the multiplier 320a, with ultrasound data from different elevational positions processed by the ADCs 318a. The delay control circuitry 324 may be configured to control the DDS circuitry 322b to add different phase offsets to the complex signals generated by the DDS circuitry 322b for multiplying, using the multiplier 320b, with ultrasound data from different elevational positions processed by the ADCs 318b. For example, if one of the ADCs 318a is configured to process ultrasound data generated by one of the ultrasound transducers 354a at the elevational position 214a of the ultrasound transducer array 256, and one of the ADCs 318a is configured to process ultrasound data generated by one of the ultrasound transducers 354 positioned at the elevational position 214b of the ultrasound transducer array 256, the delay control circuitry 324 may be configured to control the modulation circuitry 350a to add one phase offset to ultrasound data from the elevational position 214a and to add another phase offset to ultrasound data from the elevational position 214b. Thus, the delay control circuitry 324 may control the modulation circuitry 350a and the modulation circuitry 350b to implement a relative phase shift between data from each of the elevational positions.

Regarding adding different phase offsets to ultrasound data from different azimuthal positions, as described above, the ADCs 318a may be configured to convert data from the azimuthal position 212a of the ultrasound transducer array 256 and the ADCs 318b may be configured to convert data from the azimuthal position 212b of the ultrasound transducer array 256. In some embodiments, the delay control circuitry 324 may be configured to control the DDS circuitry 322a to add one phase offset to the complex signals generated by the DDS circuitry 322a for multiplying, using the multiplier 320a, with ultrasound data from the ADCs 318a, and to control the DDS circuitry 322b to add a different phase offset to the complex signals generated by the DDS circuitry 322b for multiplying, using the multiplier 320b, with ultrasound data from the ADCs 318b. Thus, the delay control circuitry 324 may control the modulation circuitry 350a and 350b to implement a relative phase shift between data from each of the azimuthal positions 212a and 212b of the ultrasound transducer array 256.

Accordingly, the delay control circuitry 324 may control the modulation circuitry 350a and 350b to implement, for given ultrasound data, a delay that is the sum of two delays, one delay corresponding to the particular elevational position from which the ultrasound data was generated, and one delay corresponding to the particular azimuthal position from which the ultrasound data was generated. As a particular example, consider three specific AFEs, each having at least one ultrasound transducer on top of it. The three AFEs will be referred to as the AFEs 208aa, 208ab, and 208ba in FIG. 2. The AFE 208aa is configured to process ultrasound data generated by ultrasound transducers 354 positioned at the azimuthal position 212a and the elevational position 214a of the ultrasound transducer array 256. The AFE 208ab is configured to process ultrasound data generated by ultrasound transducers 354 positioned at the azimuthal position 212a and the elevational position 214b of the ultrasound transducer array 256. The AFE 208a is configured to process ultrasound data generated by ultrasound transducers 354 positioned at the azimuthal position 212b and the elevational position 214a of the ultrasound transducer array 256. Let the delay for the azimuthal position 212a be $\tau_{aza}$, the delay for the azimuthal position 212b be $\tau_{azb}$, the delay for the elevational position 214a be $\tau_{ela}$, and the delay for the elevational position 214b be $\tau_{elb}$. The delay control circuitry 324 may control the modulation circuitry 350a and 350b such that ultrasound data processed by the AFE 208aa is multiplied by $e^{-i\omega_{DDS}(t-(\tau_{aza}+\tau_{ela}))}$, ultrasound data processed by the AFE 208ab is multiplied by $e^{-i\omega_{DDS}(t-(\tau_{aza}+\tau_{elb}))}$, and ultrasound data processed by the AFE 208ba is multiplied by $e^{-i\omega_{DDS}(t-(\tau_{azb}+\tau_{ela}))}$.

As described above, for generating digital sinusoidal waveforms for forming complex signals, each block of DDS circuitry 322a, 322b may include a DDS phase counter, the value of which may be used in sine and/or cosine circuits. In some embodiments that include sharing of a multiplier 320a, 320b between different ADCs 318a, 318b in different elevational positions, the DDS circuitry 322a, 322b may include multiple DDS phase counters, one for each elevational position, and each of the DDS phase counters may be initialized to a different value that, upon being used by the DDS circuitry 322a, 322b, provides the desired delay for that specific elevational position and the azimuthal position specific to the DDS circuitry 322a, 322b. When the multiplier 320a, 320b is processing data from a specific elevational position, the multiplier 320a, 320b may multiply the data by a complex signal formed based on waveforms from the DDS circuitry 322a, 322b when using that elevational position's DDS phase counter. Following the example above, when ultrasound data from the AFE 208aa is being processed, the DDS circuitry 322a may use a DDS phase counter initialized to a value that provides the delay $\tau_{aza}+\tau_{ela}$. In some embodiments that include sharing of a multiplier 320a, 320b between different ADCs 318a, 318b configured to process ultrasound data from different elevational positions, the DDS circuitry 322a, 322b may include a single DDS phase counter and an adder configured to add the DDS phase counter value to a value specific to the elevational position being processed and the azimuthal position corresponding to the DDS circuitry 322a, 322b.

For implementing a fixed delay that is determined at the beginning of ultrasound data acquisition and does not change throughout the acquisition, the fixed delay register storage circuitry 326 may have a register that stores a value for each of the elevational positions 214a-214d of the ultrasound transducer array 256 and a value for each of the azimuthal positions 212a and 212b of the ultrasound transducer array 256. When processing ultrasound data from a given elevational position and azimuthal position, the delay control circuitry 324 may be configured to retrieve the values corresponding to the elevational position and the azimuthal position from the fixed delay register storage circuitry 326. In some embodiments, the delay control circuitry 324 may be configured to provide the elevational position value to a DDS phase counter dedicated to that elevational position in the DDS circuitry 322a, 322b, as well as providing the azimuthal position value corresponding to the DDS circuitry 322a, 322b. In some embodiments, the delay control circuitry 324 may be configured to provide the elevational position and azimuthal position values to an adder configured to add the values to the value of a single DDS phase counter of the DDS circuitry 322a, 322b.

For implementing a dynamic delay that changes throughout the acquisition, in some embodiments the dynamic delay generation circuitry 334 may be configured to provide, to the delay control circuitry 324, a dynamic value corresponding to an elevational position and/or azimuthal position. The delay control circuitry 324 may be configured to add or subtract this dynamic value from one or more DDS phase counters (e.g., DDS phase counters corresponding to the elevational position and/or DDS phase counters in DDS circuitry 322 corresponding to the azimuthal position).

In some embodiments, the on-chip delay register storage circuitry (e.g., the fixed delay register storage circuitry 326 and/or the dynamic delay generation circuitry 334) may receive values for storing in its register from an external processing device, such as a mobile phone, tablet, or laptop. The ultrasound-on-chip 100 and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

The inventors have recognized that, in some embodiments, azimuthal and elevational delays (i.e., the $\tau_{az}$ and $\tau_{el}$ values described above) may be separable. In particular, while each AFE 208 in the ultrasound-on-chip 100 may require an azimuthal and elevational delay for use in processing data from each AFE 208, it may not be necessary to store in on-chip delay register storage circuitry 326 an azimuthal and elevational delay for each AFE 208, nor may be it be necessary to transmit an azimuthal and elevational delay for each AFE 208 from an external processing device to the on-chip delay register storage circuitry. While calculating all the delays to a point that a pulse coincides at that point may require a complex three-dimensional trigonometric calculation, the inventors have recognized that simply replicating a single azimuthal delay value may be used for every AFE 208 at a given azimuthal position 212a, 212b and a single elevational delay value may be used for every AFE 208 at a given elevational position 214a-214d, and this may result in focusing within an acceptable degree of error. Thus, the on-chip delay register storage circuitry may only need to receive from an external processing device azimuthal delays for every azimuthal position 212a, 212b and elevational delays for every elevational position 214a-214d, which may require significantly less time to receive than receiving an azimuthal and elevational delay value for each AFE 208. This may in turn increase the possible frame rate. The on-chip delay register storage circuitry may only need to store azimuthal delays for every azimuthal position 212a, 212b and elevational delays for every elevational position 214a-214d, which may require significantly less on-chip memory than storing an azimuthal and elevational delay value for each AFE 208. This may help reduce the amount of area on the ultrasound-on-chip 100 required for memory.

The inventors have recognized that the ultrasound-on-chip 100 may include on-chip circuitry configured to rotate azimuthal and elevational delay profiles across the ultrasound-on-chip 100 by a certain number of degrees. This may be helpful for multiplane imaging (e.g., biplane imaging). Thus, the on-chip delay register storage circuitry may receive from an external computing device and store on-chip a single profile of azimuthal and elevational delays across the AFEs 208 of the ultrasound-on-chip 100. The ultrasound-on-chip 100 may use this delay profile for imaging along one plane, and then the on-chip circuitry may rotate the delay profile (e.g., by +45 degrees, −45 degrees, +90 degrees, −90 degrees, or any other number of degrees) for imaging along another plane. This may reduce the amount of data (i.e., azimuthal and elevational delays) that the on-chip delay register storage circuitry must receive from the external computing device and also reduce the amount of data that the on-chip delay register storage circuitry must store. The on-chip circuitry configured to rotate azimuthal and elevational delay profiles may include a multiplier 320a, 320b and sine and/or cosine lookup table (LUT) circuitry in the DDS circuitry 322a, 322b.

While FIG. 3A illustrates one multiplier 320a, 320b per four ADCs 318a, 318b, this is non-limiting. In some embodiments, there may be two multipliers per four ADCs. In this example, each multiplier 320a, 320b may be clocked at four times the ADC 318a, 318b conversion rate. This may be because the multiplication step may be preceded by transformation of the real valued signal from an ADC 318a, 318b into "in phase" (real) and "out of phase" (imaginary) parts. Thus, the output of two ADCs 318a, 318b may result in two real and two imaginary signals, for a total of 4 signals that are processed at four times the ADC 318a, 318b conversion rate. Each of these signals may then pipeline into the multiplication stage of a single multiplier 320a, 320b. In some embodiments, there may be one multiplier for more or fewer than four ADCs (e.g., 1, 2, 3, 5, 6, 7, 8, or any suitable number). In some embodiments, there may be two multipliers for every two ADCs, each multiplier clocked at twice the ADC conversion rate. One multiplier may be configured to multiply the real part of the signals from the two ADCs and one multiplier may be configured to multiply the complex part of the signals from the two ADCs. In some embodiments, there may be two multipliers for every ADC, each multiplier clocked at the ADC conversion rate. One multiplier may be configured to multiply the real part of the signal from the ADC and one multiplier may be configured to multiply the complex part of the signal from the ADCs.

The filtering circuitry 328a may be configured to filter the modulated ultrasound data from the multiplier 320a. The filtering circuitry 328b may be configured to filter the modulated ultrasound data from the multiplier 320b. In some embodiments, the filtering circuitry 328a and the filtering circuitry 328b may each include a cascaded integrator-comb (CIC) filter. In some embodiments, the filtering circuitry 328a and 328b may be configured to perform decimation. In some embodiments, the filtering circuitry 328a and the filtering circuitry 328b may be configured as low-pass filters configured to remove high frequency images of the ultrasound data. As described above, the output of the modulation circuitry 350a may be a stream of ultrasound data from the ultrasound transducers 354a at the azimuthal position 212a of the ultrasound transducer array 256 that has been processed in the analog domain, digitized, modulated, and delayed, and the output of the modulation circuitry 350b may be a stream of ultrasound data from the ultrasound transducers 354b at the azimuthal position 212b of the ultrasound transducer array 256 that has been processed in the analog domain, digitized, modulated, and delayed. Thus, the output of the filtering circuitry 328a may be a stream of ultrasound data from the ultrasound transducers 354a at the azimuthal position 212a of the ultrasound transducer array 256 that has been processed in the analog domain, digitized, modulated, delayed, and filtered, and the output of the filtering circuitry 328b may be a stream of ultrasound data from the ultrasound transducers 354b at the azimuthal position 212b of the ultrasound transducer array 256 that has been processed in the analog domain, digitized, modulated, delayed, and filtered.

The summing circuitry 330 may be configured to sum the filtered ultrasound data from the filtering circuitry 328a and the filtering circuitry 328b. As described above, the output of the filtering circuitry 328a may be a stream of ultrasound data from the ultrasound transducers 354a at the azimuthal position 212a of the ultrasound transducer array 256 that has been processed in the analog domain, digitized, modulated, delayed, and filtered, and the output of the filtering circuitry 328b may be a stream of ultrasound data from the ultrasound transducers 354b at the azimuthal position 212b of the ultrasound transducer array 256 that has been processed in the analog domain, digitized, modulated, delayed, and filtered. As described above, the delay applied to ultrasound data from each of the azimuthal positions 212a and 212b of the ultrasound transducer array 256 may be different. Thus, in operation, the summing circuitry 330 may add two streams of delayed ultrasound data generated by the ultrasound transducers 354a and 354b positioned at the adjacent azimuthal positions 212a and 212b of the ultrasound transducer array 256. The delaying and summing of the two streams of ultrasound data generated by the ultrasound transducers 354a and 354b positioned at the adjacent azimuthal positions 212a and 212b of the ultrasound transducer array 256 by the receive circuitry 316A may constitute microbeamforming of the ultrasound data generated by the ultrasound transducers 354a and 354b positioned at the adjacent azimuthal positions 212a and 212b of the ultrasound transducer array 256.

Summing the ultrasound data generated by the ultrasound transducers 354a and 354b positioned at the adjacent azimuthal positions 212a and 212b of the ultrasound transducer array 256 may enable the ultrasound-on-chip 100 to transmit off-chip (i.e., from the ultrasound-on-chip 100 to a downstream electronic device, such as an FPGA or another semiconductor chip, coupled to the ultrasound-on-chip 100) half the amount of data after a pulse than the ultrasound-on-chip 100 may have transmitted if it transmitted two separate streams of ultrasound data from the azimuthal positions 212a and 212b of the ultrasound transducer array 256, without summing, after a pulse. As shown in FIG. 1, the ultrasound-on-chip 100 may include multiple UPUs 202 each having multiple azimuthal positions, and each of the UPUs 202 may each perform azimuthal summing. In embodiments in which each of the UPUs 202 on the ultrasound-on-chip 100 performs azimuthal summing, the total amount of ultrasound data that the ultrasound-on-chip 100 may need to transmit off-chip after each pulse may be less than, for instance half, the amount that the ultrasound-on-chip 100 may need to transmit off-chip without summing. Reducing the amount of data that the ultrasound-on-chip 100 transmits off-chip after each pulse may help to reduce the amount of time that it takes the ultrasound-on-chip 100 to transmit ultrasound data off-chip after every pulse, and this may enable higher pulse repetition frequency (PRF). Higher PRF may improve the ultrasound imaging by enabling faster frame rates, improved lateral resolution, and/or improved axial resolution.

In some embodiments, the summing circuitry 330 may receive two streams of n-bit data as inputs and output one stream of n-bit data as an output. Generally, however, n+1 bits are required to represent the full precision of the sum of two n-bit numbers. To reduce the n+1 bit result to n bits, in some embodiments, the summing circuitry 330 may be configured to discard the least-significant bit (LSB). In some embodiments, the summing circuitry 330 may be configured to discard the most-significant bit (MSB) and saturate by allowing the result to wrap. In some embodiments, the summing circuitry 330 may be configured to discard the MSB but saturate by clamping the result to minimum and maximum values, rather than allowing the result to wrap. In some embodiments, the summing circuitry 330 may be configured to retain the MSB and noise shape the LSB rather than discarding it. The noise shaping algorithm may include storing the LSB in a register, and when the next sample of the output stream is generated, the summing circuitry 330 may add the LSB from the previous sample into the current one. This process of capturing the LSB of the result and saving it for adding to the next result sample may repeat. This may shape the noise by moving the quantization error signal into higher frequencies which may then be low-pass filtered downstream (not illustrated).

As described above, the receive circuitry illustrated in FIG. 3A may be included in a single UPU 202 in the ultrasound-on-chip 100. As there may be multiple instances of UPUs 202 on the ultrasound-on-chip 100, there may be multiple instances of the receive circuitry illustrated in FIG. 3A in the ultrasound-on-chip 100. It should also be appreciated that the receive circuitry illustrated in FIG. 3A shows two groups of circuitry (i.e., analog processing circuitry 352a, 352b, ADCs 318a, 318b, modulation circuitry 350a, 350b and filtering circuitry 328a, 328b), each of which is configured to process ultrasound data from one of two azimuthal positions 212a and 212b in the UPU 202. However, if the UPU 202 includes more than two azimuthal positions, there may be correspondingly more than two copies of this circuitry.

Figure 3B:
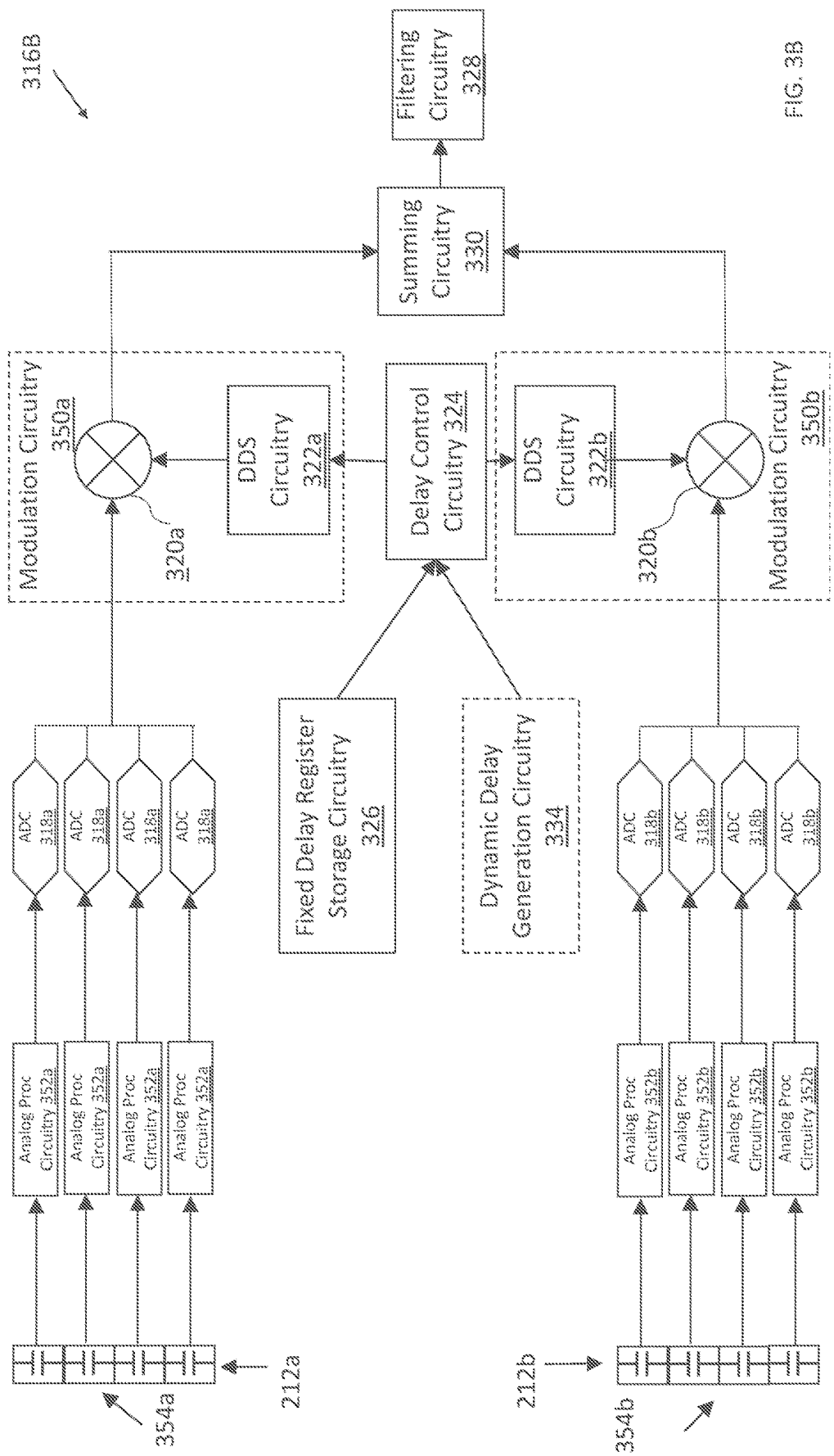
FIG. 3B is a block diagram illustrating example receive circuitry in an ultrasound device, in accordance with certain embodiments described herein.

FIG. 3B is a block diagram illustrating example receive circuitry 316B in an ultrasound device, in accordance with certain embodiments described herein. FIG. 3B is the same as FIG. 3A, except that the receive circuitry 316B performs summing by the summing circuitry 300 prior to filtering by filtering circuitry 328.

Figure 3C:
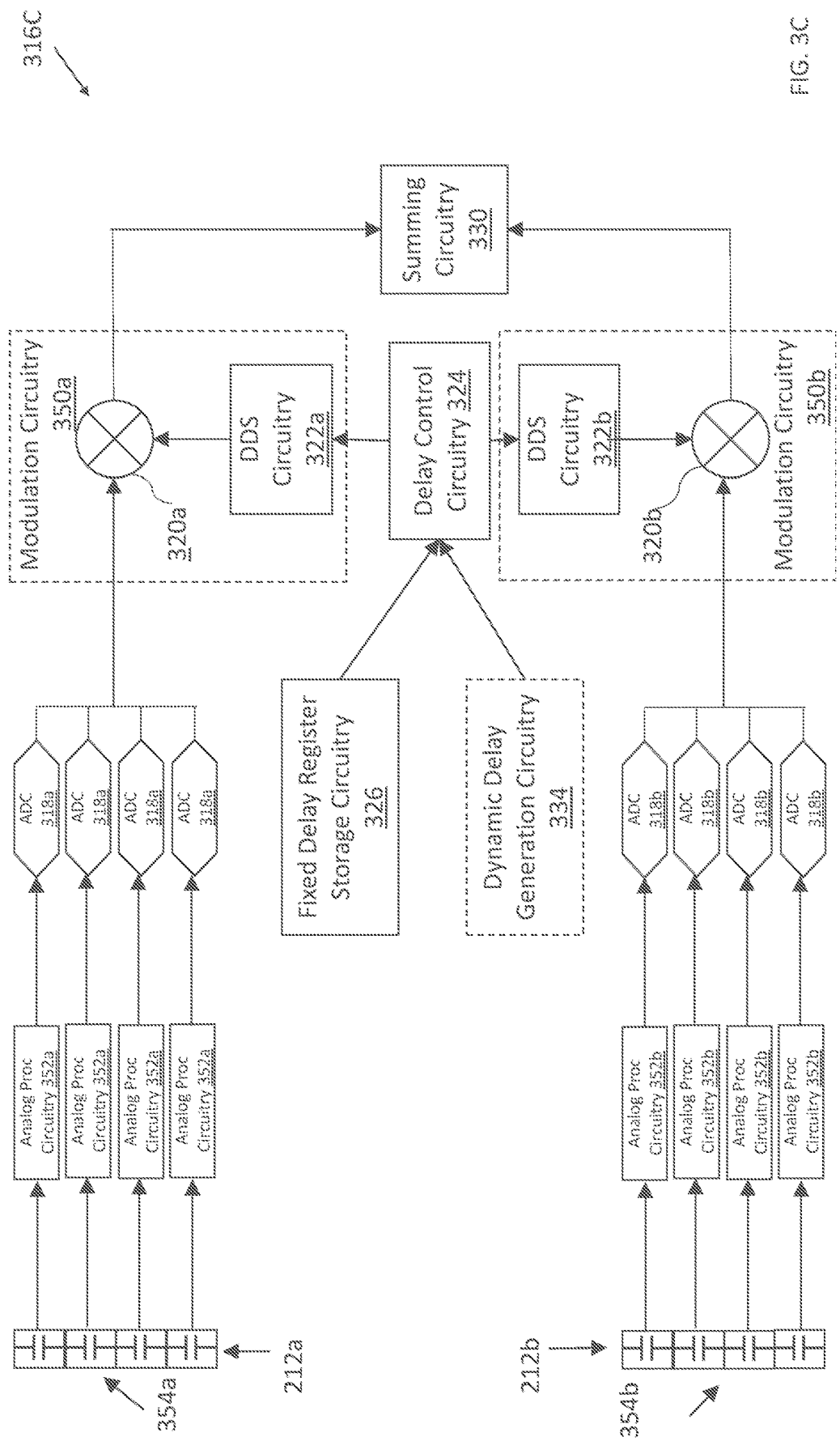
FIG. 3C is a block diagram illustrating example receive circuitry in an ultrasound device, in accordance with certain embodiments described herein.

FIG. 3C is a block diagram illustrating example receive circuitry 316C in an ultrasound device, in accordance with certain embodiments described herein. FIG. 3C is the same as FIG. 3C, except that the receive circuitry 316C does not perform filtering by filtering circuitry. The receive circuitry 316C may be appropriate, for example, when decimation is not performed by the receive circuitry 316C.

Figure 4:
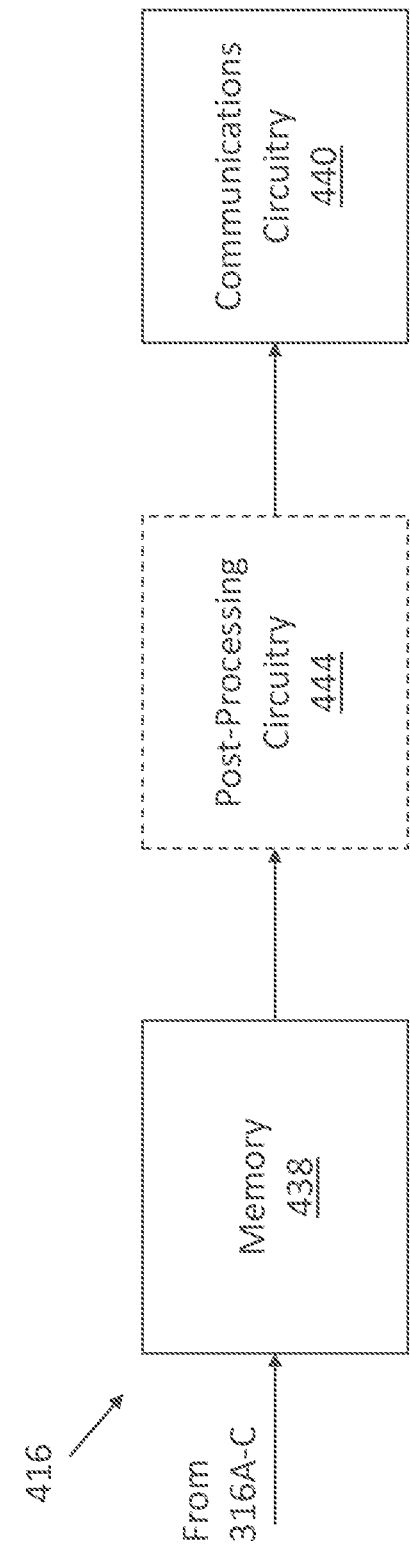
FIG. 4 is a block diagram illustrating example receive circuitry in an ultrasound device, in accordance with certain embodiments described herein.

FIG. 4 is a block diagram illustrating example receive circuitry 416 in an ultrasound device, in accordance with certain embodiments described herein. The receive circuitry 416 is downstream of the receive circuitry 316A, 316B, or 316C of FIGS. 3A-C. The receive circuitry 416 includes memory 438, post-processing circuitry 444, and communications circuitry 440. As illustrated, the input of the memory 438 is coupled to an output of the receive circuitry 316A, 316B, or 316C. In some embodiments, the output of the summing circuitry 330 may be directly coupled to the input of the memory 438, while in other embodiments, there may be other circuitry between the summing circuitry 330 and the memory 438. The output of the memory 438 is coupled to the input of the post-processing circuitry 444. The output of the post-processing circuitry 444 is coupled to the input of the communications circuitry 440. In some embodiments, the post-processing circuitry 444 may be absent, and the output of the memory 438 may be coupled, directly or with intervening circuitry, to the input of the communications circuitry 440. For this reason, the post-processing circuitry is shown in dashed lines.

The memory 438 may be configured to store the ultrasound data after processing by the receive circuitry 316A, 316B, or 316C. In some embodiments, the memory 438 may be configured as a static random-access memory (SRAM), although other types of memory may be used. The post-processing circuitry 444 may be configured to post-process ultrasound data and may include, for example, circuitry for summing, requantization, noise shaping, waveform removal, image formation, and/or backend processing. The communications circuitry 440 may be configured to transmit data over a communications link to a separate electronic device (e.g., field-programmable gate array (FPGA) device or one or more other semiconductor chips). For example, the communications circuitry 440 may include circuitry capable of transmitting data over a Universal Serial Bus (USB) communications link, a serial-deserializer (SerDes) communications link, a double data rate (DDR) communications link, or a wireless communications link (e.g., a link employing the IEEE 802.11 standard). The separate electronic device may be disposed within the ultrasound device that includes the ultrasound-on-chip 100 (e.g., a handheld ultrasound probe, a wearable ultrasound patch, or an ingestible ultrasound pill) or it may be an external electronic device to which the ultrasound device is coupled (e.g., a phone, a tablet, or a laptop).

As described above, microbeamforming of ultrasound data from adjacent azimuthal positions (e.g., the azimuthal positions 212a and 212b of the ultrasound transducer array 256) may help to reduce the amount of data that the communications circuitry 440 must transfer from the ultrasound-on-chip 100 to the separate electronic device after each pulse, and thereby reduce the amount of time required for the communications circuitry 440 to transfer data from the ultrasound-on-chip 100 to the separate electronic device after each pulse. This may help to enable higher pulse repetition frequency (PRF).

Figure 5:
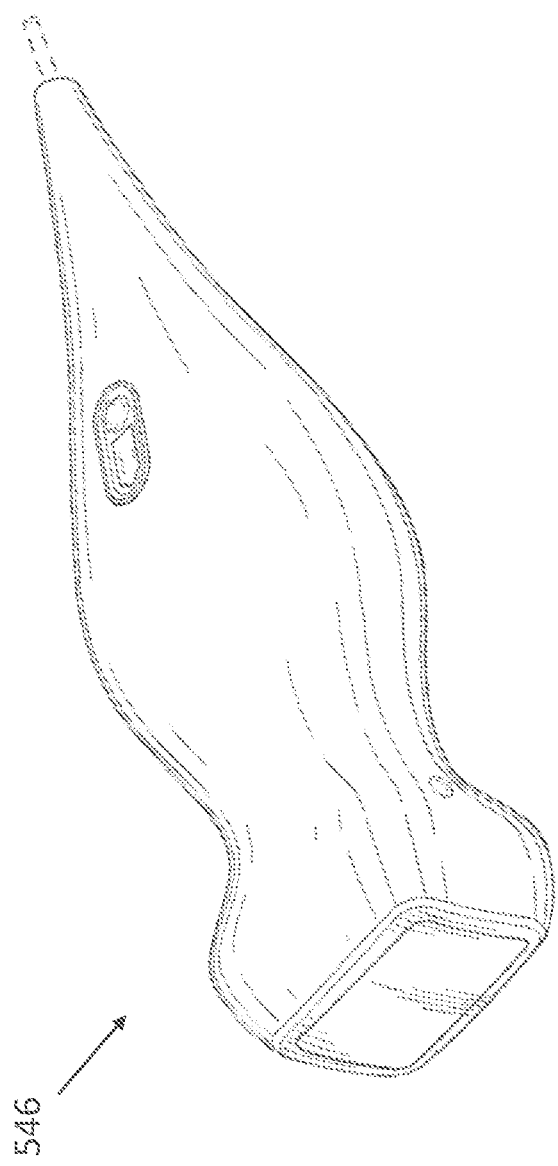
FIG. 5 illustrates an example handheld ultrasound probe, in accordance with certain embodiments described herein.

FIG. 5 illustrates an example handheld ultrasound probe 546, in accordance with certain embodiments described herein. In some embodiments, the ultrasound-on-chip 100 may be disposed in the handheld ultrasound probe 546. Thus, in some embodiments in which the receive circuitry 316A, 316B, or 316C is disposed on the ultrasound-on-chip 100, all of the receive circuitry 316A, 316B, or 316C, including the ADCs 318a, the ADCs 318b, the multiplier 320a, the multiplier 320b, the DDS circuitry 322a, the DDS circuitry 322b, the delay control circuitry 324, the fixed delay register storage circuitry 326, the dynamic delay generation circuitry 334 (when implemented in the receive circuitry 316A, 316B, or 316C), the filtering circuitry 328a, the filtering circuitry 328b, and the summing circuitry 330 may be disposed in the handheld ultrasound probe 546. In some embodiments, portions of the receive circuitry 316A, 316B, or 316C may be disposed in the handheld ultrasound probe 546. Additionally, in some embodiments in which the receive circuitry 416 is disposed on the ultrasound-on-chip 100, all of the receive circuitry 416, including the memory 438, the post-processing circuitry 444 (when implemented in the receive circuitry 416), and the communications circuitry 440, may be disposed in the handheld ultrasound probe 546, while in some embodiments, portions of the receive circuitry 316A, 316B, or 316C may be disposed in the handheld ultrasound probe 546.

Figure 6:
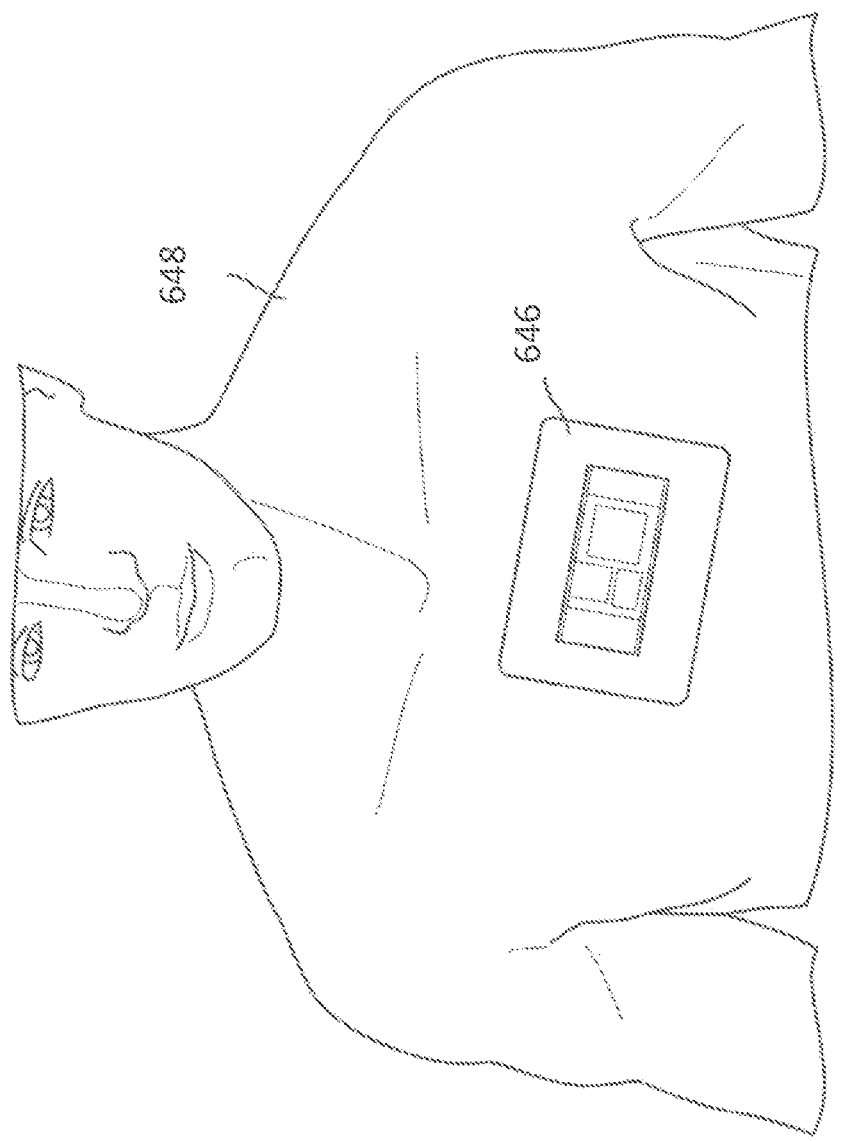
FIG. 6 illustrates an example wearable ultrasound patch, in accordance with certain embodiments described herein.

FIG. 6 illustrates an example wearable ultrasound patch 646, in accordance with certain embodiments described herein. The wearable ultrasound patch 646 is coupled to a subject 648. In some embodiments, the ultrasound-on-chip 100 may be disposed in the wearable ultrasound patch 646. Thus, in some embodiments in which the receive circuitry 316A, 316B, or 316C is disposed on the ultrasound-on-chip 100, all of the receive circuitry 316A, 316B, or 316C, including the ADCs 318a, the ADCs 318b, the multiplier 320a, the multiplier 320b, the DDS circuitry 322a, the DDS circuitry 322b, the delay control circuitry 324, the fixed delay register storage circuitry 326, the dynamic delay generation circuitry 334 (when implemented in the receive circuitry 316A, 316B, or 316C), the filtering circuitry 328a, the filtering circuitry 328b, and the summing circuitry 330 may be disposed in the wearable ultrasound patch 646. In some embodiments, portions of the receive circuitry 316A, 316B, or 316C may be disposed in the wearable ultrasound patch 646. Additionally, in some embodiments in which the receive circuitry 416 is disposed on the ultrasound-on-chip 100, all of the receive circuitry 416, including the memory 438, the post-processing circuitry 444 (when implemented in the receive circuitry 416), and the communications circuitry 440, may be disposed in the wearable ultrasound patch 646, while in some embodiments, portions of the receive circuitry 416 may be disposed in the wearable ultrasound patch 646.

Figure 7:
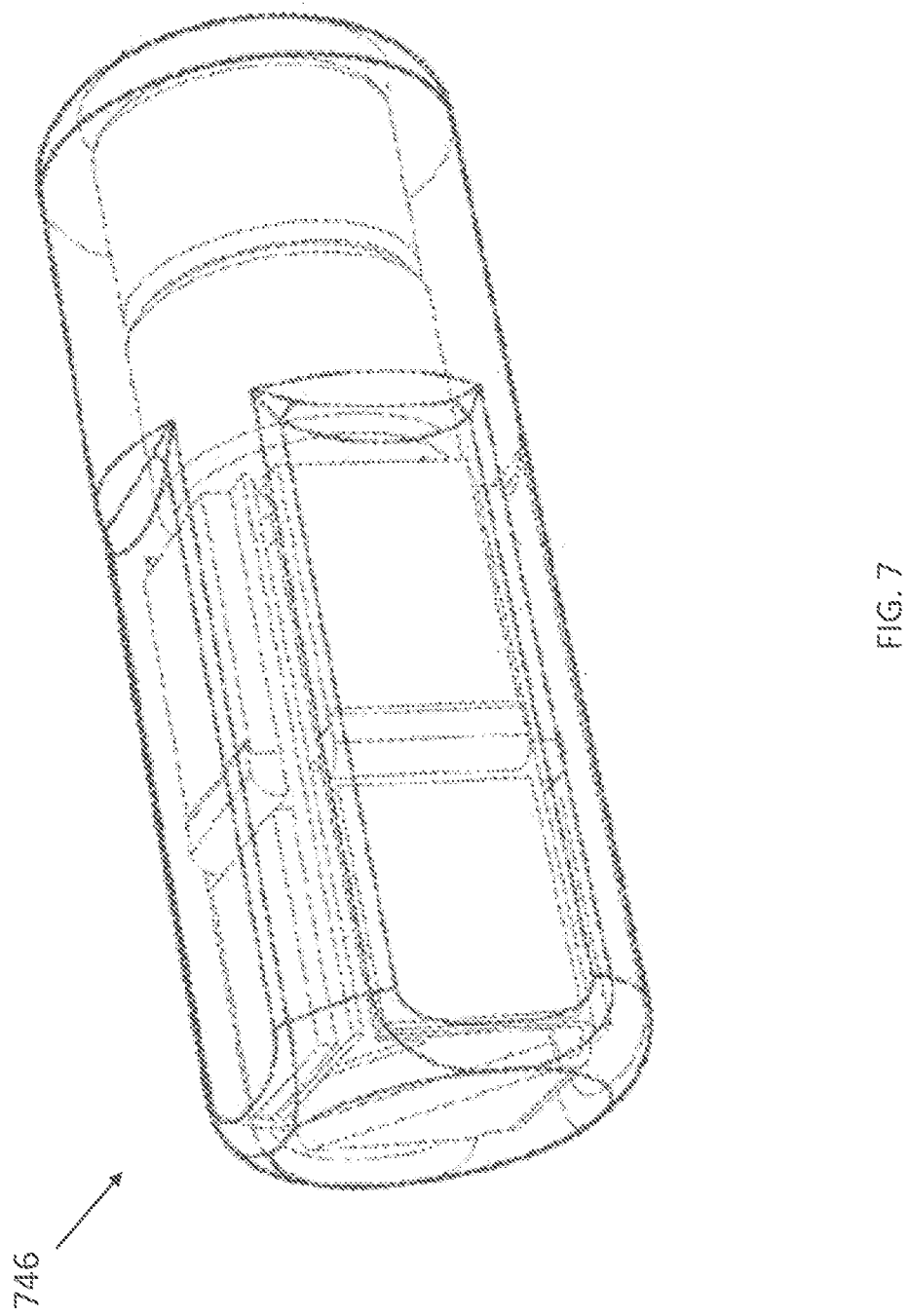
FIG. 7 illustrates an example ingestible ultrasound pill, in accordance with certain embodiments described herein.

FIG. 7 illustrates an example ingestible ultrasound pill 746, in accordance with certain embodiments described herein. In some embodiments, the ultrasound-on-chip 100 may be disposed in the ingestible ultrasound pill 746. Thus, in some embodiments in which the receive circuitry 316A, 316B, or 316C is disposed on the ultrasound-on-chip 100, all of the receive circuitry 316A, 316B, or 316C, including the ADCs 318a, the ADCs 318b, the multiplier 320a, the multiplier 320b, the DDS circuitry 322a, the DDS circuitry 322b, the delay control circuitry 324, the fixed delay register storage circuitry 326, the dynamic delay generation circuitry 334 (when implemented in the receive circuitry 316A, 316B, or 316C), the filtering circuitry 328a, the filtering circuitry 328b, and the summing circuitry 330 may be disposed in the ingestible ultrasound pill 746. In some embodiments, portions of the receive circuitry 316A, 316B, or 316C may be disposed in the ingestible ultrasound pill 746. Additionally, in some embodiments in which the receive circuitry 416 is disposed on the ultrasound-on-chip 100, all of the receive circuitry 416, including the memory 438, the post-processing circuitry 444 (when implemented in the receive circuitry 416), and the communications circuitry 440, may be disposed in the ingestible ultrasound pill 746, while in some embodiments, portions of the receive circuitry 316A, 316B, or 316C may be disposed in the ingestible ultrasound pill 746.

Further description of the handheld ultrasound probe 546, the wearable ultrasound patch 646, and the ingestible ultrasound pill 746 may be found in U.S. patent application Ser. No. 15/626,711 titled "UNIVERSAL ULTRASOUND DEVICE AND RELATED APPARATUS AND METHODS," filed on Jun. 19, 2017 and published as U.S. Pat. App. Publication No. 2017-0360399 A1 (and assigned to the assignee of the instant application).

Figure 8:
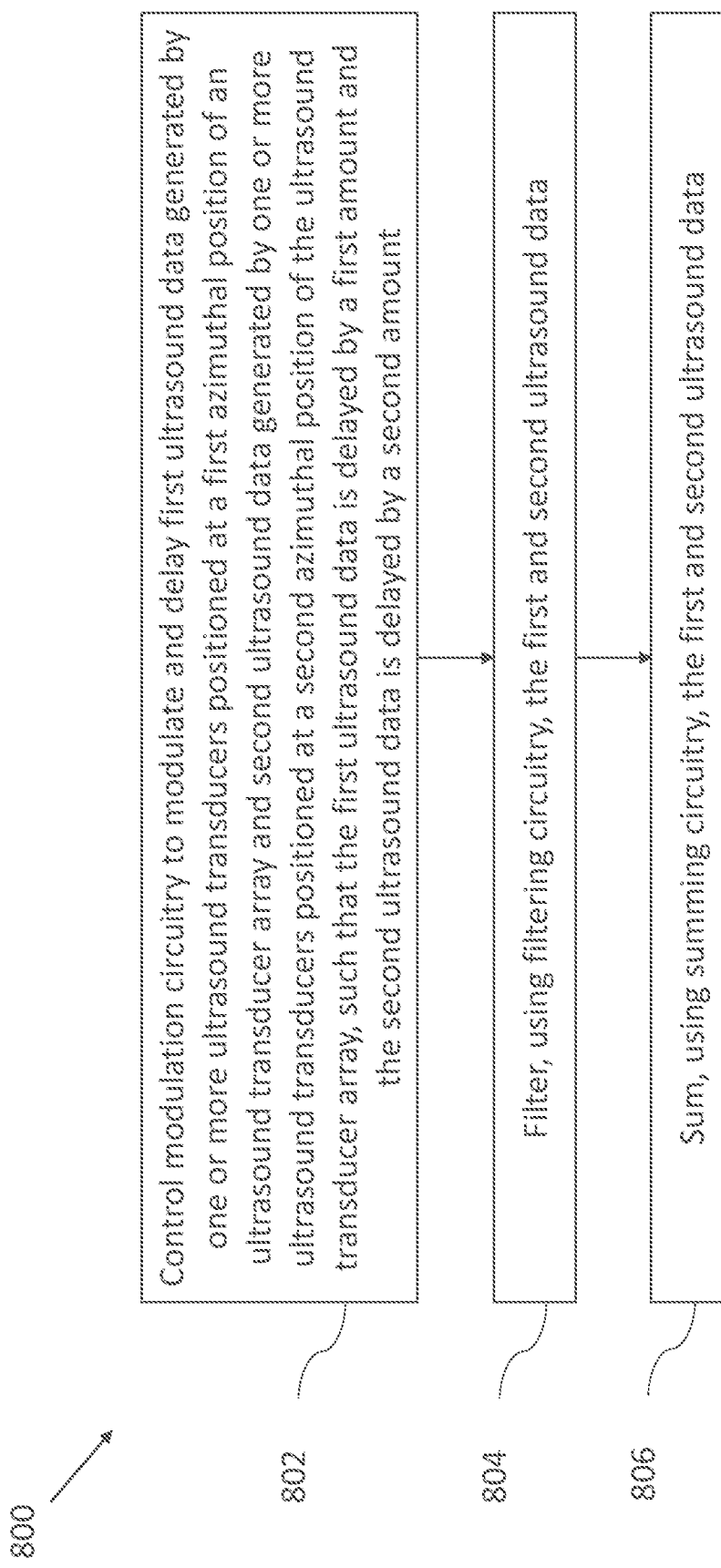
FIG. 8 illustrates a process for processing ultrasound data, in accordance with certain embodiments described herein.

FIG. 8 illustrates a process 800 for processing ultrasound data, in accordance with certain embodiments described herein. The process 800 may be performed by receive circuitry (e.g., the receive circuitry 316A, 316B, or 316C) on an ultrasound-on-chip (e.g., the ultrasound-on-chip 100) in an ultrasound device (e.g., the handheld ultrasound probe 546, the wearable ultrasound patch 646, or the ingestible ultrasound pill 746). Further description of the ultrasound-on-chip may be found with reference to the ultrasound-on-chip 100.

In act 802, control circuitry (e.g., the DDS control circuitry 324) controls the receive circuitry to modulate and delay, using modulation circuitry (e.g., the modulation circuitry 350a and 350b), first ultrasound data generated by one or more ultrasound transducers (e.g., the ultrasound transducers 354a) positioned at a first azimuthal position (e.g., the azimuthal position 212a) of an ultrasound transducer array (e.g., the ultrasound transducer array 256) and second ultrasound data generated by one or more ultrasound transducers (e.g., the ultrasound transducers 354b) positioned at a second azimuthal position (e.g., the azimuthal position 212b) of the ultrasound transducer array, such that the first ultrasound data is delayed by a first amount and the second ultrasound data is delayed by a second amount. Further description of act 802 may be found with reference to the modulation circuitry 350a and 350b). It should be appreciated that the receive circuitry may have performed additional processing between generation of the ultrasound data by the ultrasound transducers and the modulating and delaying at act 802. For example, analog processing circuitry (e.g., the analog processing circuitry 352a and 352b) may have performed analog processing in the analog domain and/or ADCs (e.g., the ADCs 318a and 318b) may have performed digital conversion.

In act 804, the receive circuitry filters, using filtering circuitry (e.g., the filtering circuitry 328a and 328b), the first and second ultrasound data. Further description of act 804 may be found with reference to the filtering circuitry 328a and 328b.

In act 806, the receive circuitry sums, using summing circuitry (e.g., the summing circuitry 330), the first and second ultrasound data. Further description of act 806 may be found with reference to the summing circuitry 330. The delaying (at act 802) and the summing (at act 806) of the first and second ultrasound data generated by the ultrasound transducers positioned at the first and second azimuthal positions of the ultrasound transducer array may constitute microbeamforming of the first and second ultrasound data generated by the ultrasound transducers positioned at the first and second azimuthal positions of the ultrasound transducer array, respectively.

Summing the ultrasound data from the first and second azimuthal positions of the ultrasound transducer array may enable the ultrasound-on-chip to transmit off-chip (i.e., from the ultrasound-on-chip to a downstream electronic device, such as an FPGA or another semiconductor chip, coupled to the ultrasound-on-chip) half the amount of data after a pulse than the ultrasound-on-chip may have transmitted if it transmitted two separate streams of ultrasound data from the first and second azimuthal positions, without summing, after a pulse. The ultrasound-on-chip may include multiple UPUs each having multiple azimuthal positions, and each of the UPUs may perform azimuthal summing. In embodiments in which each of the UPUs on the ultrasound-on-chip performs azimuthal summing, the total amount of ultrasound data that the ultrasound-on-chip may need to transmit off-chip after each pulse may be half the amount of data that the ultrasound-on-chip 100 may need to transmit off-chip without summing. Reducing the amount of data that the ultrasound-on-chip 100 transmits off-chip after each pulse may help to reduce the amount of time that it takes the ultrasound-on-chip 100 to transmit ultrasound data off-chip after every pulse, and this may enable higher pulse repetition frequency (PRF). Higher PRF may improve the ultrasound imaging by enabling faster frame rates, improved lateral resolution, and/or improved axial resolution.

In some embodiments, the filtering of act 804 may be performed after the summing of act 806. In some embodiments, the filtering of act 804 may not be performed.

It should be appreciated that the DDS circuitry described above may include local oscillators (LO), numerically controlled oscillators (NCO), heterodyning circuits, and/or software defined radios. Such circuitry may be implemented as sine/cosine look up table(s) (LUT) with constant or variable phase increments (i.e., the address LUT step size), and/or such circuitry may be implemented with on-the-fly computation of cosine/sine at each phase increment (e.g., a coordinate rotation digital computer (CORDIC)).

Some aspects relate to a method of controlling, using control circuitry, modulation circuitry to modulate and delay first ultrasound data generated by first ultrasound transducers positioned at a first azimuthal position of an ultrasound transducer array of an ultrasound device and second ultrasound data generated by second ultrasound transducers positioned at a second azimuthal position of the ultrasound transducer array of the ultrasound device, such that the first ultrasound data is delayed by a first delay amount and the second ultrasound data is delayed by a second delay amount that is different from the first delay amount; filtering, using filtering circuitry, the first and second ultrasound data received from the modulation circuitry; and summing, using summing circuitry, the first and second ultrasound data received from the filtering circuitry; wherein the ultrasound transducer array, the control circuitry, the modulation circuitry, the filtering circuitry, and the summing circuitry are integrated onto a semiconductor chip or one or more semiconductor chips packaged together.

In some embodiments, controlling the modulation circuitry to modulate and delay the first ultrasound data generated by the first ultrasound transducers and the second ultrasound data generated by the second ultrasound transducers such that the first ultrasound data is delayed by the first delay amount and the second ultrasound data is delayed by the second delay amount comprises controlling the modulation circuitry to multiply the first ultrasound data by $e^{-i\omega_{DDS}(t-\tau_1)}$ and multiply the second ultrasound data by $e^{-i\omega_{DDS}(t-\tau_2)}$, where $\tau_1$ is the first delay amount, $\tau_2$ is the second delay amount, $\omega_{DDS}$ is a center frequency, and t is a time variable.

In some embodiments, the first delay amount is a sum of two delays, one delay corresponding to an elevational position of the ultrasound transducer array from which the first ultrasound data was generated and one delay corresponding to the first azimuthal position of the ultrasound transducer array.

In some embodiments, the method further comprises rotating a delay profile across the ultrasound transducer array by a certain number of degrees.

In some embodiments the method further comprises performing multiplane imaging by using the delay profile for imaging along a first imaging plane, rotating the delay profile, and using the rotated delay profile for imaging along a second imaging plane.

In some embodiments, the method further comprises performing noise shaping when summing the first and second ultrasound data.

In some embodiments, the method further comprises transmitting an output of the summing circuitry off the semiconductor chip or the one or more semiconductor chips packaged together.

Some aspects relate to an ultrasound device, comprising an ultrasound transducer array comprising first ultrasound transducers positioned at a first azimuthal position of the ultrasound transducer array; and second ultrasound transducers positioned at a second azimuthal position of the ultrasound transducer array; modulation circuitry; control circuitry configured to control the modulation circuitry to modulate and delay first ultrasound data generated by the first ultrasound transducers and second ultrasound data generated by the second ultrasound transducers such that the first ultrasound data is delayed by a first delay amount and the second ultrasound data is delayed by a second delay amount that is different from the first delay amount; summing circuitry configured to sum the first and second ultrasound data received from the modulation circuitry; wherein the ultrasound transducer array, the control circuitry, the modulation circuitry, and the summing circuitry are integrated onto a semiconductor chip or one or more semiconductor chips packaged together.

Some aspects relate to a method of controlling, using control circuitry, modulation circuitry to modulate and delay first ultrasound data generated by first ultrasound transducers positioned at a first azimuthal position of an ultrasound transducer array of an ultrasound device and second ultrasound data generated by second ultrasound transducers positioned at a second azimuthal position of the ultrasound transducer array of the ultrasound device, such that the first ultrasound data is delayed by a first delay amount and the second ultrasound data is delayed by a second delay amount that is different from the first delay amount; summing, using summing circuitry, the first and second ultrasound data received from the modulation circuitry; wherein the ultrasound transducer array, the control circuitry, the modulation circuitry, the filtering circuitry, and the summing circuitry are integrated onto a semiconductor chip or one or more semiconductor chips packaged together.

Various aspects of the present application may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone or in any combination. For example, aspects described in one embodiment may be combined in any manner with aspects described in other embodiments. The disclosure is therefore not limited in its application to the details and arrangement of components set forth in the foregoing text or illustrated in the drawings.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An ultrasound device comprising:
   a semiconductor chip or a package of one or more semiconductor chips integrating each of the following:
      an ultrasound transducer array having:
         a first plurality of ultrasound transducers positioned at a first position of the ultrasound transducer array and configured to generate first ultrasound data; and
         a second plurality of ultrasound transducers positioned at a second position of the ultrasound transducer array and configured to generate second ultrasound data;
      modulation circuitry configured to modulate the first ultrasound data and the second ultrasound data such that the first ultrasound data is delayed by a first delay and the second ultrasound data is delayed by a second delay;
      filtering circuitry configured to filter the first and second ultrasound data received from the modulation circuitry; and summing circuitry configured to sum the first and second ultrasound data received from the filtering circuitry.

2. The ultrasound device according to claim 1, wherein the modulation circuitry includes a multiplier and direct digital synthesis (DDS) circuitry.

3. The ultrasound device according to claim 2, wherein the DDS circuitry generates a digital sinusoidal waveform to form a complex signal.

4. The ultrasound device according to claim 3, wherein modulating the first ultrasound data further includes multiplying the first ultrasound data by the complex signal.

5. The ultrasound device according to claim 3, wherein the complex signal includes one of the first delay or the second delay, a center frequency, and a time variable.

6. The ultrasound device according to claim 1, wherein the first position is a first azimuthal position and the second position is a second azimuthal position different from the first azimuthal position.

7. The ultrasound device according to claim 6, wherein the first plurality of ultrasound transducers is positioned at the first azimuthal position and different elevational positions of the ultrasound transducer array, and the first ultrasound data comprises a stream of data having, at a given time, a value of ultrasound data from a subset of the first plurality of ultrasound transducers at one elevational position of the different elevational positions.

8. The ultrasound device according to claim 6, wherein the modulation circuitry is configured to use the first delay for every elevational position at the first azimuthal position of the ultrasound transducer array and to use the second delay for every elevational position at the second azimuthal position of the ultrasound transducer array.

9. The ultrasound device according to claim 1, wherein the modulation circuitry is further configured to implement a relative phase shift between the first ultrasound data and the second ultrasound data.

10. The ultrasound device according to claim 1, wherein the semiconductor chip or the package of one or more semiconductor chips further integrates delay register storage circuitry.

11. The ultrasound device according to claim 10, wherein the modulation circuitry is further configured to retrieve the first delay and the second delay from the delay register storage circuitry.

12. The ultrasound device according to claim 1, wherein the modulation circuitry is further configured to rotate a delay profile across the ultrasound transducer array by a certain number of degrees.

13. The ultrasound device according to claim 1, wherein the ultrasound device is configured to perform multiplane imaging by using a delay profile for imaging along a first imaging plane, rotating the delay profile, and using the rotated delay profile for imaging along a second imaging plane.

14. The ultrasound device according to claim 1, wherein the summing circuitry is further configured to perform noise shaping when summing the first and second ultrasound data.

\* \* \* \* \*